United States Patent
Suzuki et al.

(10) Patent No.: US 8,258,361 B2
(45) Date of Patent: Sep. 4, 2012

(54) TRANSITION METAL COMPLEX COMPOUNDS, OLEFIN OLIGOMERIZATION CATALYSTS INCLUDING THE COMPOUNDS, AND PROCESSES FOR PRODUCING OLEFIN OLIGOMERS USING THE CATALYSTS

(75) Inventors: Yasuhiko Suzuki, Sodegaura (JP); Shinsuke Kinoshita, Ichihara (JP); Atsushi Shibahara, Chiba (JP); Naritoshi Yoshimura, Ichihara (JP); Isao Hara, Ninomiya (JP); Tetsuya Hamada, Ichihara (JP); Kazumori Kawamura, Chiba (JP); Kou Tsurugi, Ichihara (JP); Yasunori Saito, Ichihara (JP); Seiichi Ishii, Ichihara (JP); Yasushi Nakayama, Ichihara (JP); Naoto Matsukawa, Ichihara (JP); Susumu Murata, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 311 days.

(21) Appl. No.: 12/452,438

(22) PCT Filed: Jun. 27, 2008
(Under 37 CFR 1.47)

(86) PCT No.: PCT/JP2008/061740
§ 371 (c)(1),
(2), (4) Date: Dec. 30, 2009

(87) PCT Pub. No.: WO2009/005003
PCT Pub. Date: Jan. 8, 2009

(65) Prior Publication Data
US 2011/0082325 A1    Apr. 7, 2011

(30) Foreign Application Priority Data

Jul. 4, 2007  (JP) .................... 2007/176026

(51) Int. Cl.
*C07C 2/22*    (2006.01)
*C07F 7/28*    (2006.01)
*B01J 31/18*   (2006.01)

(52) U.S. Cl. ........ 585/513; 585/500; 585/502; 585/510; 585/511; 585/512; 585/520; 585/521; 585/522; 585/523; 585/524; 502/103; 502/118; 502/123; 502/124; 556/32; 556/51; 556/54; 556/56

(58) Field of Classification Search .......... 502/103, 502/111, 123, 124, 118; 556/32, 51, 54, 556/56; 585/500, 502, 520, 521, 522, 523, 585/524, 510, 511, 512, 513

See application file for complete search history.

(56) References Cited

U.S. PATENT DOCUMENTS

| | | | |
|---|---|---|---|
| 4,892,851 | A | 1/1990 | Ewen et al. |
| 4,990,640 | A | 2/1991 | Tsutsui et al. |
| 5,155,080 | A | 10/1992 | Elder et al. |
| 5,158,920 | A | 10/1992 | Razavi |
| 5,321,106 | A | 6/1994 | LaPointe |
| 5,387,568 | A | 2/1995 | Ewen et al. |
| 5,519,100 | A | 5/1996 | Ewen et al. |

(Continued)

FOREIGN PATENT DOCUMENTS

JP    1-501950    7/1989

(Continued)

OTHER PUBLICATIONS

Simpson, et al., "Ethylene Polymers, LLDPE" in Encyclopedia of Polymer Science and Technology, John Wiley & Sons, available on-line Oct. 22, 2001.*

(Continued)

*Primary Examiner* — In Suk Bullock
*Assistant Examiner* — Bradley Etherton
(74) *Attorney, Agent, or Firm* — Foley & Lardner LLP

(57) ABSTRACT

The invention provides transition metal complex compounds, high-activity olefin oligomerization catalysts containing the compounds, and olefin oligomerization processes using the catalysts.
A transition metal complex compound [A] according to the invention is represented by Formula (I) or Formula (I') below. An olefin oligomerization catalyst includes the transition metal complex compound [A]. In an olefin oligomerization process of the invention, an olefin is oligomerized in the presence of the catalyst.

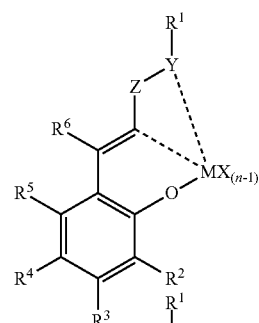

(I)

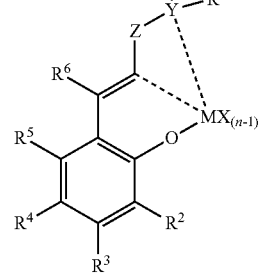

(I')

15 Claims, 9 Drawing Sheets

U.S. PATENT DOCUMENTS

| | | | |
|---|---|---|---|
| 5,614,457 A | 3/1997 | Ewen et al. | |
| 5,663,249 A | 9/1997 | Ewen et al. | |
| 5,856,257 A | 1/1999 | Freeman et al. | |
| 6,201,076 B1 * | 3/2001 | Etherton et al. | 526/74 |
| 7,049,378 B2 * | 5/2006 | Ittel et al. | 526/161 |
| 7,056,995 B2 | 6/2006 | Deckers et al. | |
| 7,291,575 B2 * | 11/2007 | Shih | 502/158 |
| 2004/0087436 A1 * | 5/2004 | Gibson et al. | 502/150 |
| 2005/0004331 A1 * | 1/2005 | Sun et al. | 526/129 |
| 2005/0209420 A1 * | 9/2005 | Solan et al. | 526/172 |

FOREIGN PATENT DOCUMENTS

| | | |
|---|---|---|
| JP | 1-502036 | 7/1989 |
| JP | 2-78687 | 3/1990 |
| JP | 3-179005 | 8/1991 |
| JP | 3-179006 | 8/1991 |
| JP | 3-207703 | 9/1991 |
| JP | 3-207704 | 9/1991 |
| JP | 2003-268030 | 9/2003 |
| JP | 2004-524959 | 8/2004 |
| WO | WO 88/05792 A1 | 8/1988 |
| WO | WO 88/05793 A1 | 8/1988 |
| WO | WO 01/44324 A2 | 6/2001 |
| WO | WO 01/68572 A1 | 9/2001 |

OTHER PUBLICATIONS

Knight, et al., "Problems and Solutions for Alkene Polymerization Catalysts Incorporating Schiff-Bases; Migratory Insertion and Radical Mechanisms of Catalyst Deactivation" in Chem. Comm., 4 (2002) 352-353—month unknown.*

Andes et al., "New Tantalum-Based Catalyst System for the Selective Trimerization of Ethene to 1-Hexene," Journal of American Chemical Society, vol. 123, No. 30, Aug. 1, 2001, pp. 7423-7424.

Dixon et al., "Advances in selective ethylene trimerisation—a critical overview," Journal of Organometallic Chemistry, 2004, vol. 689, Issue 23, Nov. 15, 2004, pp. 3641-3668.

Hu et al., "Synthesis and Characterization of Novel Tridentate [NOP] Titanium Complexes and Their Application to Copolymerization and Polymerization of Ethylene," Organometallics, vol. 23, No. 8, Apr. 12, 2004, pp. 1684-1688.

Pennington et al., "The synthesis, structure and ethene polymerisation catalysis of mono(salicylaldiminato) titanium and zirconium complexes," Dalton Transaction, 2005, pp. 561-571,—2005.

Wang et al., "Synthesis and Characterization of Titanium(IV) Complexes Bearing Monoanionic [O¯NX] (X = O, S, Se) Tridentate Ligands and Their Behaviors in Ethylene Homo- and Copolymerization with 1-Hexene," Organometallics, vol. 25, No. 13, Jun. 19, 2006, pp. 3259-3266.

Korean Office Action issued in connection with the corresponding application No. 10-2010-7002504, dated Aug. 18, 2011, 5 pages.

Yasuhiko Suzuki et al., "Recent Advances in Phenoxy-Based Catalysts for Olefin Polymerization", Bulletin of the Chemical Society of Japan, vol. 76 (2003), No. 8, pp. 1493-1517.

Shen, Yu-Mei et al., "Chemical Fixation of Carbon Dioxide Catalyzed by Binaphthyldiamino Zn, Cu, and Co Salen-Type Complexes," Journal of Organic Chemistry, 2003, vol. 68, No. 4, pp. 1559-1562—2003.

* cited by examiner

[FIG. 1]
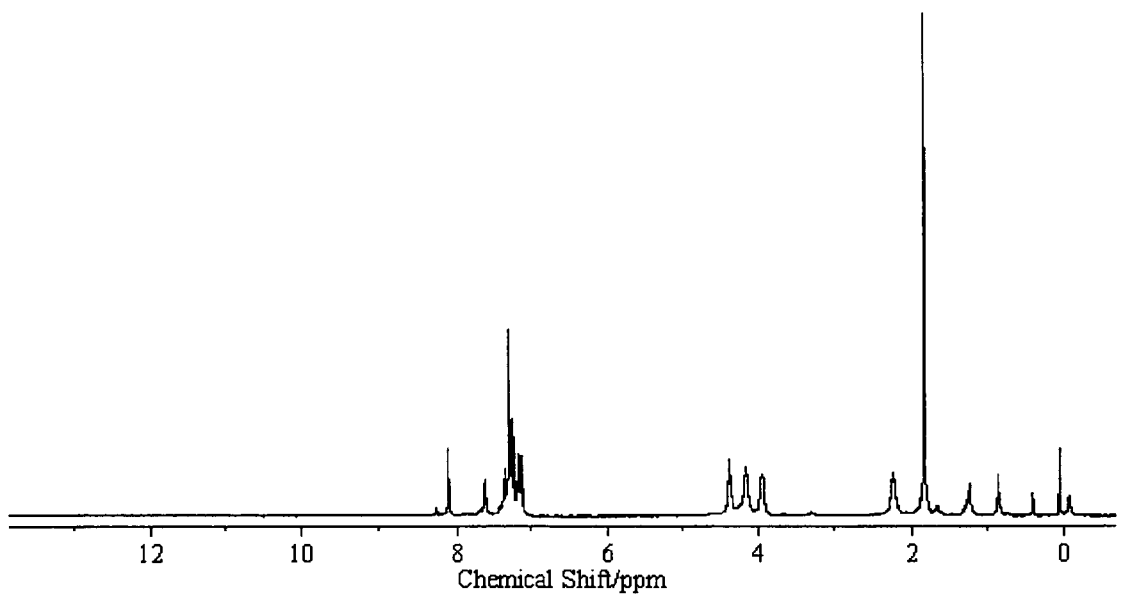

[FIG. 2]
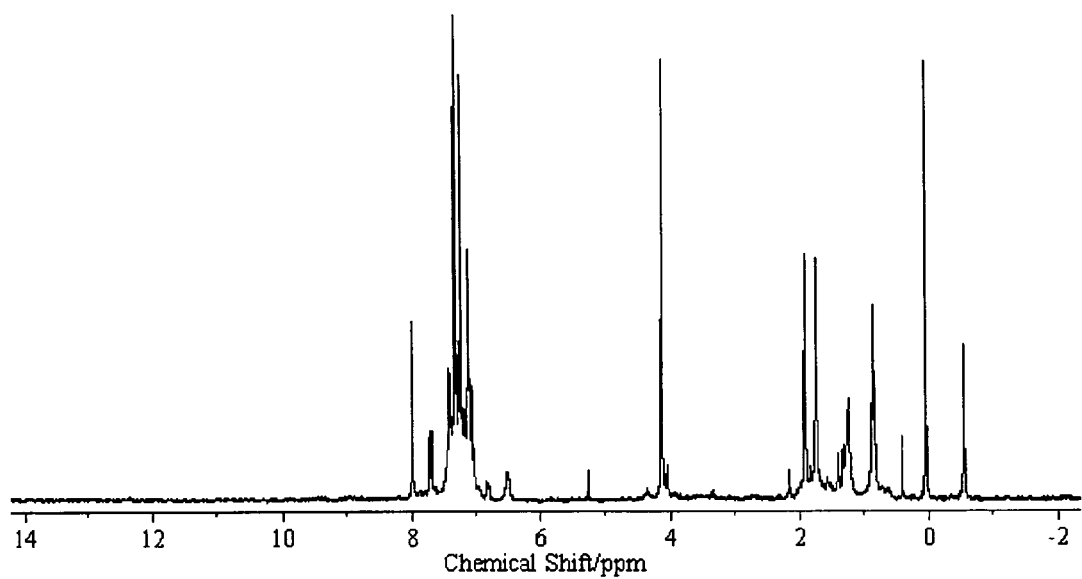

[FIG. 3]
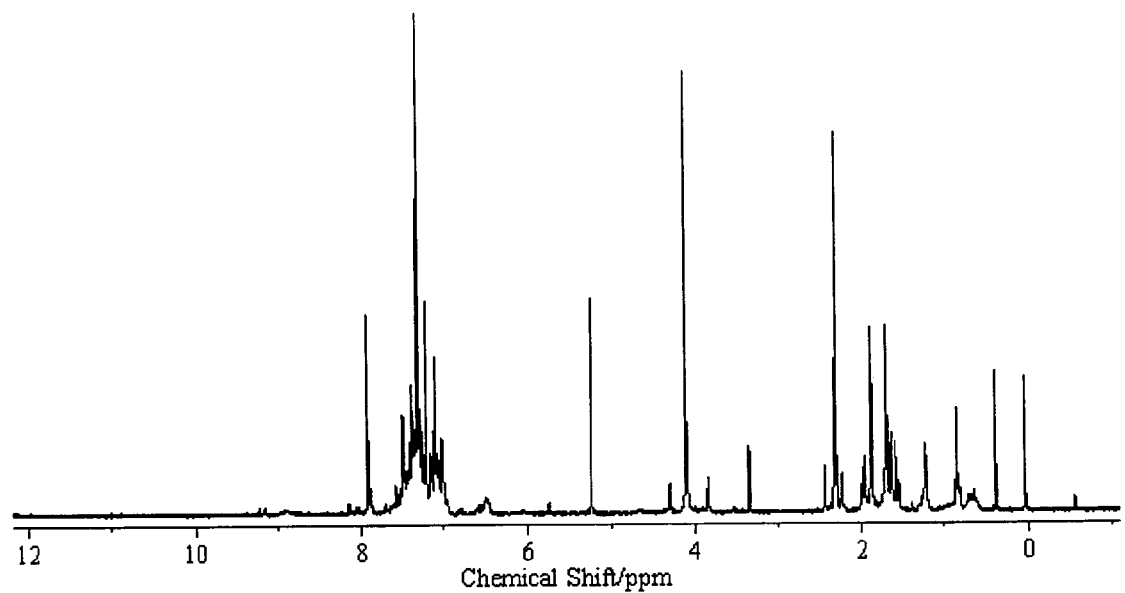

[FIG. 4]
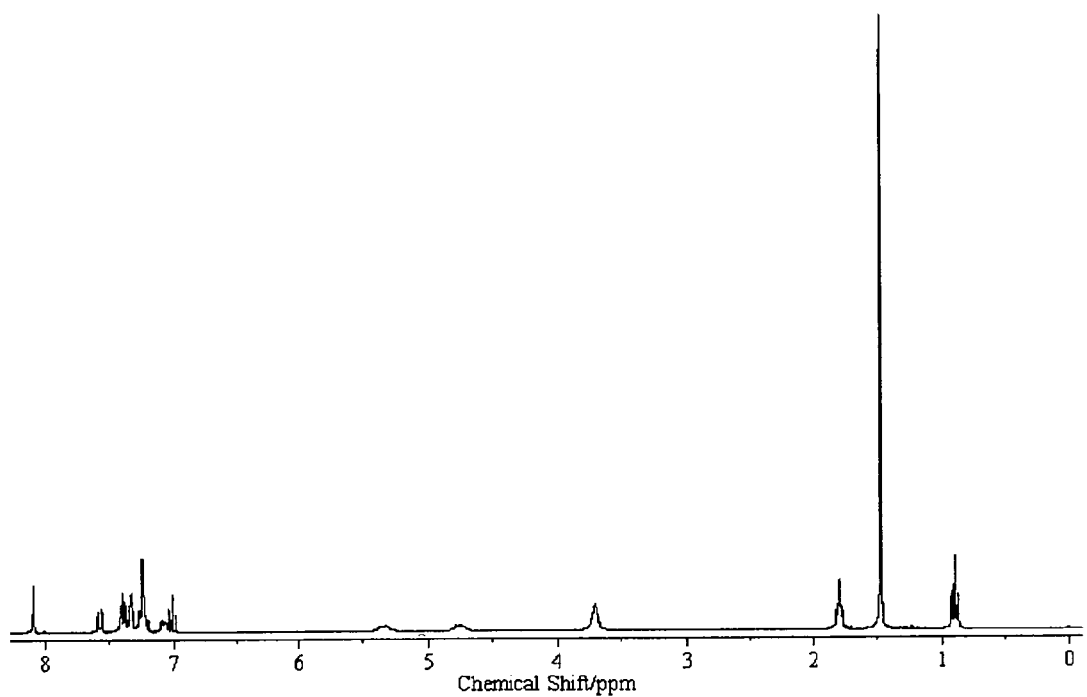

[FIG. 5]
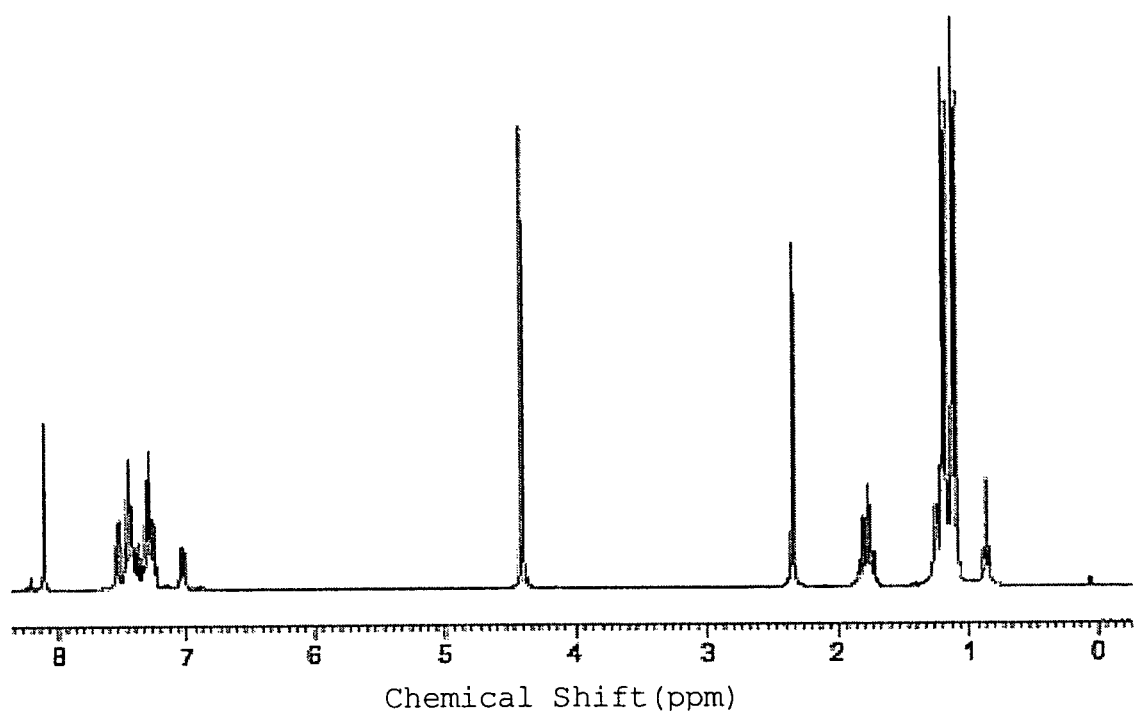

[FIG. 6]
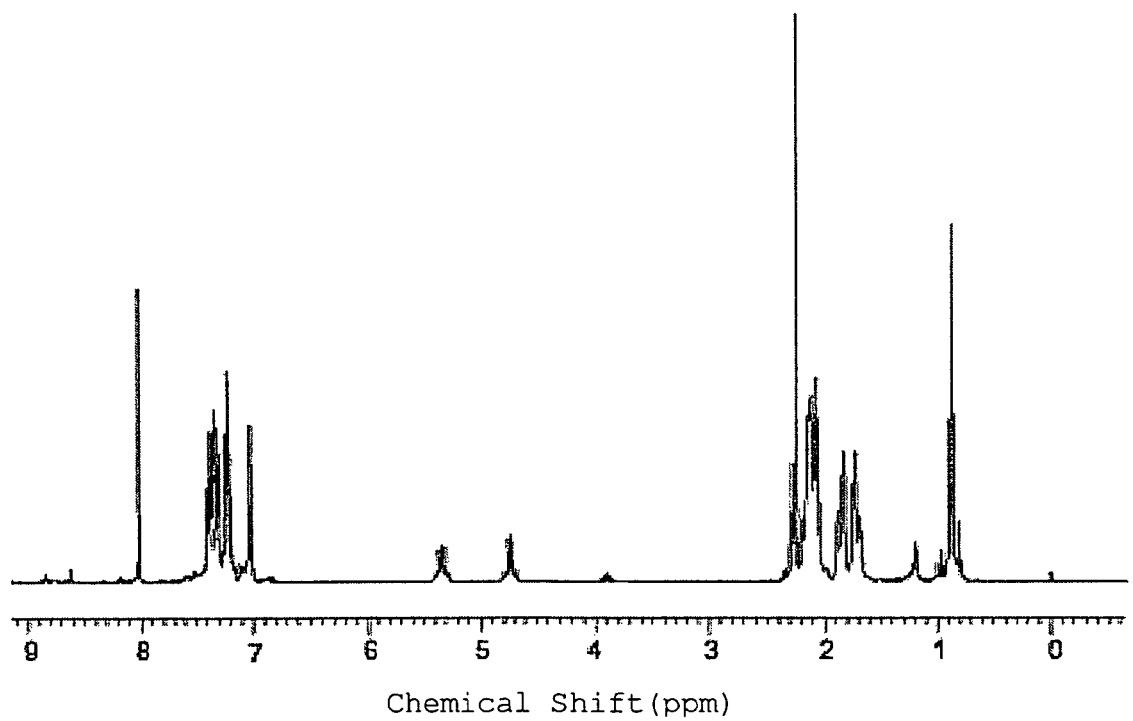
Chemical Shift(ppm)

[FIG. 7]
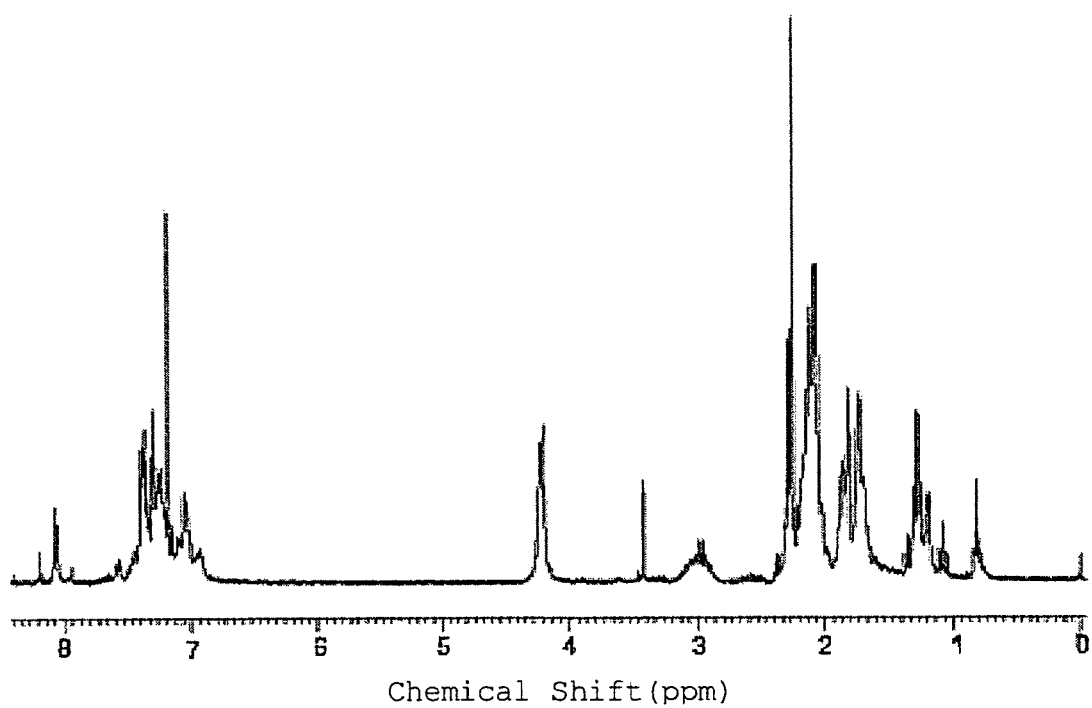

[FIG. 8]
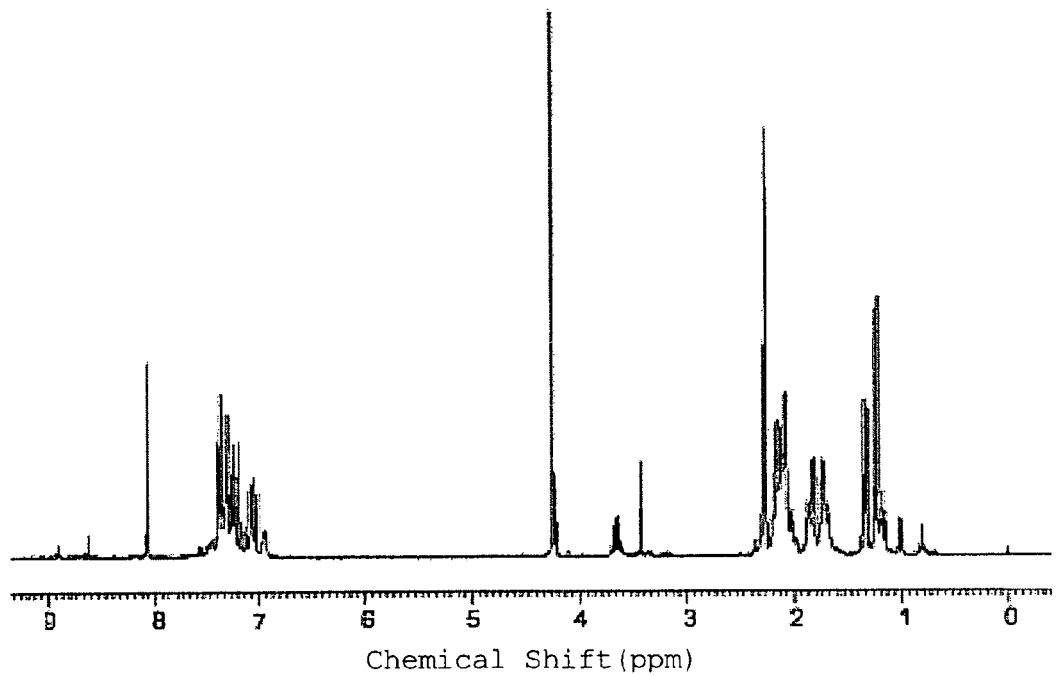

[FIG. 9]
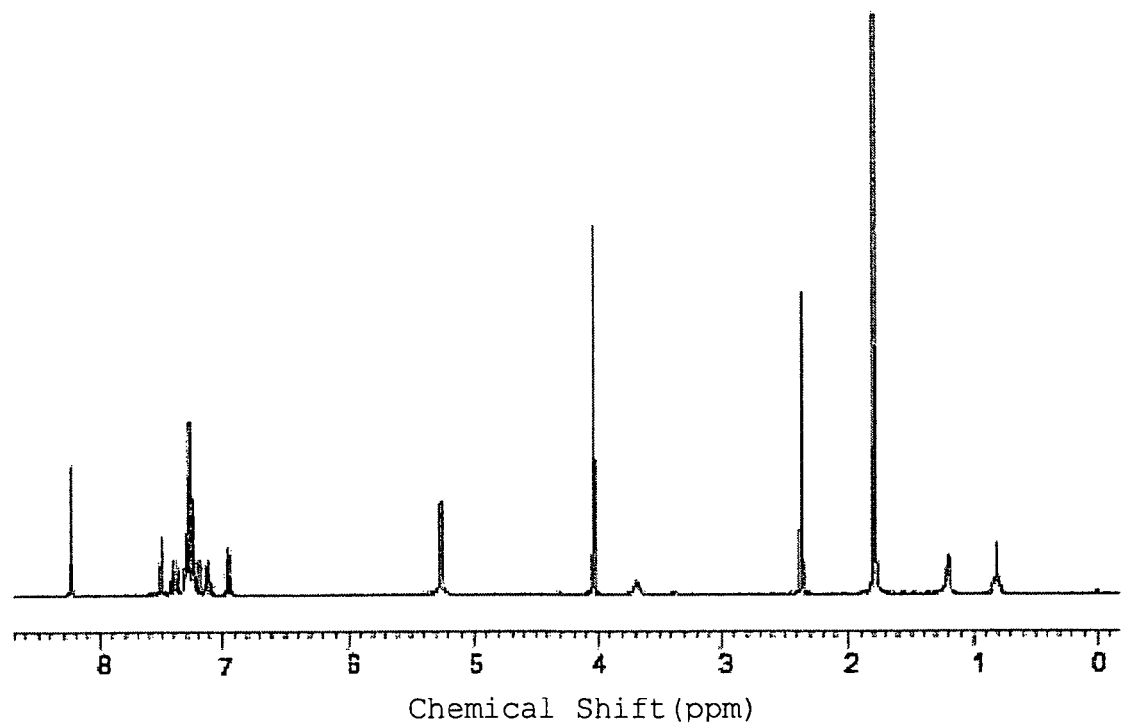

TRANSITION METAL COMPLEX COMPOUNDS, OLEFIN OLIGOMERIZATION CATALYSTS INCLUDING THE COMPOUNDS, AND PROCESSES FOR PRODUCING OLEFIN OLIGOMERS USING THE CATALYSTS

FIELD OF THE INVENTION

The present invention relates to transition metal complex compounds, olefin oligomerization catalysts including the compounds, and processes of producing olefin oligomers with the catalysts.

BACKGROUND OF THE INVENTION

Industrial olefin oligomerization is most often catalyzed by organoaluminum compounds or transition metal compounds. The oligomerization of ethylene in particular gives a mixture of α-olefins. Of the α-olefins, 1-hexene has a high demand as a material for polyolefins, and high-selectivity processes for 1-hexene are desired. The only selective process that has been used in the industry is trimerization of ethylene using chromium compounds (Patent Document 1). This process affords approximately 8 kg of 1-hexene per 1 mmol chromium atom-hour under an ethylene pressure of 100 bar. However, it is preferred that a higher activity is achieved under a lower pressure so that the costs for pressure and catalyst in the production can be reduced. Further, very few techniques have been reported for the production of 1-hexene by trimerizing ethylene with transition metal compounds other than chromium compounds (Patent Documents 2 and 3, Non-Patent Documents 1 and 2).

Patent Document 1: U.S. Pat. No. 5,856,257

Patent Document 2: JP-A-2004-524959

Patent Document 3: WO 01/68572

Non-Patent Document 1: Journal of American Chemical Society, 2001, Vol. 123, pp. 7423-7424

Non-Patent Document 2: Journal of Organometallic Chemistry, 2004, Vol. 689, pp. 3641-3668

SUMMARY OF THE INVENTION

The present invention has been made in view of the aforementioned problems in the art. It is therefore an object of the invention to provide novel transition metal complex compounds, olefin oligomerization catalysts of superior activity containing the compounds, and processes for producing olefin oligomers in the presence of the olefin oligomerization catalysts.

The present inventors studied diligently to solve the problems in the art. They have then found that olefin oligomerization catalysts containing a transition metal complex compound with a specific structure show excellent activity and are suited for use in olefin oligomerization. In particular, the catalysts are capable of catalyzing the oligomerization of ethylene as a starting material to afford a trimer of ethylene, i.e., 1-hexene, with high selectivity. The present invention has been completed based on the findings.

The present invention relates to the following [1] to [17].

[1] A transition metal complex compound [A] represented by Formula (I) below:

[Chem. 1]

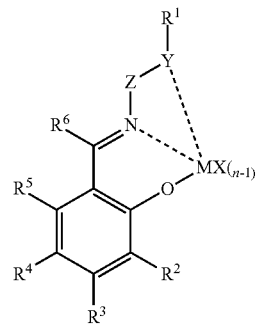

(I)

wherein $R^1$ to $R^6$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, two or more of $R^1$ to $R^6$ may be linked to each other, and $R^1$ may be linked to Z;

M is a transition metal atom of Group 3 to Group 10 of the periodic table;

n is a valence of M;

X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, the atoms or groups indicated by X may be the same or different from each other, and the groups indicated by X may be linked to each other to form a ring;

Y is an oxygen atom, a nitrogen atom, a phosphorus atom or a sulfur atom;

Z is a hydrocarbon group or a heterocyclic compound residue that may have a substituent group, and the minimum number of bonds linking Y with N is in the range of 4 to 6;

the bond between Y and Z may be a double bond or a triple bond, and the bond between Y and $R^1$ may be a double bond or a triple bond; and the dotted lines each denote a coordination bond.

[2] The transition metal complex compound [A] described in [1], wherein the minimum number of bonds linking Y with N in the transition metal complex compound of Formula (I) is 5 or 6.

[3] The transition metal complex compound [A] described in [1], wherein Y, N and Z in the transition metal complex compound of Formula (I) form a structure represented by Formula (II) below:

[Chem. 2]

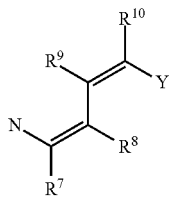

(II)

wherein Y is an oxygen atom, a nitrogen atom, a phosphorus atom or a sulfur atom; and $R^7$ to $R^{10}$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and when $R^7$ to $R^{10}$ are hydrocarbon groups, $R^7$ and $R^8$ may be linked to each other to form a ring and $R^9$ and $R^{10}$ may be linked to each other to form a ring.

[4] The transition metal complex compound [A] described in any one of [1] to [3], wherein M in the transition metal complex compound of Formula (I) is a transition metal atom of Group 4 of the periodic table, and n is 4.

[5] A transition metal complex compound [A] represented by Formula (I') below:

[Chem. 3]

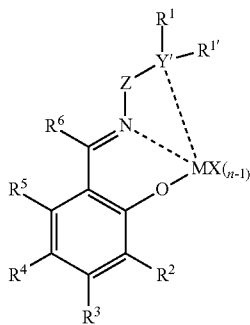

(I')

wherein $R^1$ to $R^6$ and $R^{1'}$ are the same or different from each other and are each a hydrogen-atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, two or more of $R^{1'}$ and $R^1$ to $R^6$ may be linked to each other, and $R^1$ may be linked to Z;

M is a transition metal atom of Group 3 to Group 10 of the periodic table;

n is a valence of M;

X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, the atoms or groups indicated by X may be the same or different from each other, and the groups indicated by X may be linked to each other to form a ring;

Y' is a nitrogen atom or a phosphorus atom;

Z is a hydrocarbon group or a heterocyclic compound residue that may have a substituent group, and the minimum number of bonds linking Y' with N is in the range of 4 to 6; and the dotted lines each denote a coordination bond.

[6] The transition metal complex compound [A] described in [5], wherein the minimum number of bonds linking Y' with N in the transition metal complex compound of Formula (I') is 5 or 6.

[7] The transition metal complex compound [A] described in [5], wherein Y', N and Z in the transition metal complex compound of Formula (I') form a structure represented by Formula (II') below:

[Chem. 4]

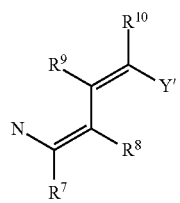

(II')

wherein Y' is a nitrogen atom or a phosphorus atom; and $R^7$ to $R^{10}$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and when $R^7$ to $R^{10}$ are hydrocarbon groups, $R^7$ and $R^9$ may be linked to each other to form a ring and $R^9$ and $R^{10}$ may be linked to each other to form a ring.

[8] The transition metal complex compound [A] described in anyone of [5] to [7], wherein M in the transition metal complex compound of Formula (I') is a transition metal atom of Group 4 of the periodic table, and n is 4.

[9] An olefin oligomerization catalyst comprising the transition metal complex compound. [A] described in any one of [1] to [8].

[10] The olefin oligomerization catalyst described in [9], wherein the catalyst comprises:

[A] the transition metal complex compound; and

[B] at least one compound selected from the group consisting of (b-1) an organometallic compound, (b-2) an organoaluminum oxy-compound and (b-3) a compound which reacts with the transition metal complex compound [A] to form an ion pair.

[11] The olefin oligomerization catalyst described in [9], wherein the catalyst comprises:

[A] the transition metal complex compound;

[B] at least one compound selected from the group consisting of (b-1) an organometallic compound, (b-2) an organoaluminum oxy-compound and (b-3) a compound which reacts with the transition metal complex compound [A] to form an ion pair; and

[C] a carrier to support at least one compound selected from [A] and [B].

[12] A process for producing an olefin oligomer, comprising oligomerizing an olefin in the presence of the olefin oligomerization catalyst described in any one of [9] to [11].

[13] A process for producing an olefin oligomer, comprising oligomerizing an olefin in the presence of the olefin oligomerization catalyst described in any one of [9] to [11] and with a C5-7 linear saturated hydrocarbon as a solvent.

[14] A process for producing an olefin oligomer, comprising oligomerizing an olefin in the presence of the olefin oligomerization catalyst described in any one of [9] to [11] and hydrogen.

[15] A process for producing an olefin oligomer, comprising oligomerizing an olefin in the presence of the olefin oligomerization catalyst described in any one of [9] to [11] and an antistatic agent.

[16] The process described in any one of [12] to [15], wherein the olefin is ethylene.

[17] The process described in any one of [12] to [15], wherein the olefin is ethylene and the olefin oligomer is 1-hexene.

ADVANTAGES OF THE INVENTION

The transition metal complex compounds according to the present invention and the olefin oligomerization catalysts including the compounds have high activity. The processes for producing olefin oligomers according to the present invention use the olefin oligomerization catalysts. The processes enable the oligomerization of ethylene into 1-hexene with high activity and high selectivity, providing very high industrial values.

BRIEF DESCRIPTION OF THE DRAWINGS

FIG. 1 is a $^1$H NMR spectrum of Compound 2.
FIG. 2 is a $^1$H NMR spectrum of Compound 5.
FIG. 3 is a $^1$H NMR spectrum of Compound 7.
FIG. 4 is a $^1$H NMR spectrum of Compound 22.
FIG. 5 is a $^1$H NMR spectrum of Compound 30.
FIG. 6 is a $^1$H NMR spectrum of Compound 31.
FIG. 7 is a $^1$H NMR spectrum of Compound 33.
FIG. 8 is a $^1$H NMR spectrum of Compound 34.
FIG. 9 is a $^1$H NMR spectrum of Compound 36.

BEST MODE FOR CARRYING OUT THE INVENTION

The transition metal complex compounds, the olefin oligomerization catalysts and the processes of producing olefin oligomers using the olefin oligomerization catalysts according to the present invention will be described in detail hereinbelow.

In the invention, the olefin oligomerization refers to the production of dimers to decamers of olefins.

An olefin oligomerization catalyst according to the invention includes a transition metal complex compound [A] described later. The olefin oligomerization catalyst usually contains, in addition to the transition metal complex compound [A], at least one compound [B] selected from the group consisting of (b-1) an organometallic compound, (b-2) an organoaluminum oxy-compound and (b-3) a compound which reacts with the transition metal complex compound [A] to form an ion pair. The compound (b-3) which reacts with the transition metal complex compound [A] to form an ion pair is also referred to as the ionizing ionic compound in the invention.

The olefin oligomerization catalyst may contain a carrier [C] to support at least one compound selected from [A] and [B].

[Transition Metal Complex Compounds [A]]

The transition metal complex compounds [A] in the invention have two embodiments. The transition metal complex compounds in the first embodiment are represented by Formula (I) below:

[Chem. 5]

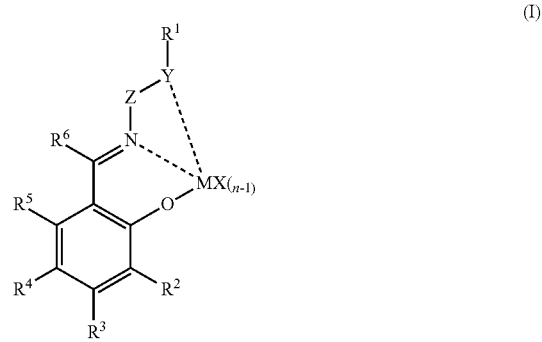

(I)

In Formula (I), $R^1$ to $R^6$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group. Two or more of $R^1$ to $R^6$ may be linked to each other, and $R^1$ may be linked to Z.

More specifically, $R^1$ to $R^6$ are each preferably a hydrogen atom, a halogen atom, a hydrocarbon group, a heterocyclic compound residue, a hydrocarbon-substituted silyl group, a hydrocarbon-substituted siloxy group, an alkoxy group, an alkylthio group, an aryloxy group, an arylthio group, an acyl group, an ester group, a thioester group, an amide group, an imide group, an amino group, an imino group, a sulfonate group, a sulfonamide group, a cyano group, a nitro group, a carboxyl group, a sulfo group, a mercapto group, an aluminum-containing group or a hydroxyl group.

Examples of the halogen atoms include fluorine, chlorine, bromine and iodine.

Examples of the hydrocarbon groups include linear or branched alkyl groups of 1 to 30, preferably 1 to 20, and more preferably 1 to 10 carbon atoms such as methyl, ethyl, n-propyl, isopropyl, n-butyl, isobutyl, sec-butyl, tert-butyl, neopentyl and n-hexyl; linear or branched alkenyl groups of 2 to 30, and preferably 2 to 20 carbon atoms such as vinyl, allyl and isopropenyl; linear or branched alkynyl groups of 2 to 30, and preferably 2 to 20 carbon atoms such as ethynyl and propargyl; cyclic saturated hydrocarbon groups of 3 to 30, and preferably 3 to 20 carbon atoms such as cyclopropyl, cyclobutyl, cyclopentyl, cyclohexyl and adamantyl; cyclic unsaturated hydrocarbon groups of 5 to 30 carbon atoms such as cyclopentadienyl, indenyl and fluorenyl; aryl groups of 6 to 30, and preferably 6 to 20 carbon atoms such as phenyl, naphthyl, biphenyl, terphenyl, phenanthryl and anthracenyl; alkyl-substituted aryl groups such as tolyl, isopropylphenyl, t-butylphenyl, dimethylphenyl and di-t-butylphenyl; and alkylidene groups of 1 to 30, and preferably 5 to 10 carbon atoms such as benzylidene, methylidene and ethylidene.

The hydrocarbon groups may have hydrogen atoms substituted with halogens. Examples of such substituted groups include halogenated hydrocarbon groups of 1 to 30, and preferably 1 to 20 carbon atoms such as trifluoromethyl, pentafluorophenyl and chlorophenyl.

The hydrocarbon groups may have hydrogen atoms substituted with other hydrocarbon groups. Examples of such groups include aryl-substituted alkyl groups such as benzyl, cumyl, diphenylethyl and trityl.

The hydrocarbon groups may have heterocyclic compound residues; oxygen-containing groups such as alkoxy groups, aryloxy groups, ester groups, ether groups, acyl groups, carboxyl groups, carbonate groups, hydroxyl groups, peroxy groups and carboxylic anhydride groups; nitrogen-containing groups such as amino groups, imino groups, amide groups, imide groups, hydrazino groups, hydrazono groups, nitro groups, nitroso groups, cyano groups, isocyano groups, cyanate groups, amidino groups, diazo groups and amino groups in ammonium salt form; boron-containing groups such as boranediyl groups, boranetriyl groups and diboranyl groups; sulfur-containing groups such as mercapto groups, thioester groups, dithioester groups, alkylthio groups, arylthio groups, thioacyl groups, thioether groups, thiocyanate groups, isothiocyanate groups, sulfonate groups, sulfonamide groups, thiocarboxyl groups, dithiocarboxyl groups, sulfo groups, sulfonyl groups, sulfinyl groups and sulfenyl groups; phosphorus-containing groups such as phosphide groups, phosphoryl groups, thiophosphoryl groups and phosphate groups; silicon-containing groups; germanium-containing groups; and tin-containing groups.

Of these, particularly preferred groups are linear or branched alkyl groups of 1 to 30, preferably 1 to 20, more preferably 1 to 10, and still more preferably 2 to 10 carbon atoms such as methyl, ethyl, n-propyl, isopropyl, n-butyl, isobutyl, sec-butyl, t-butyl, neopentyl, n-hexyl and adamantyl; aryl groups of 6 to 30, and preferably 6 to 20 carbon atoms such as phenyl, naphthyl, biphenyl, terphenyl, phenanthryl and anthracenyl; and substituted aryl groups wherein the above aryl groups are substituted with 1 to 5 substituent groups such as halogen atoms, alkyl or alkoxy groups of 1 to 30, and preferably 1 to 20 carbon atoms, and aryl or aryloxy groups of 6 to 30, and preferably 6 to 20 carbon atoms.

Examples of the heterocyclic compound residues include residues of nitrogen-containing compounds such as pyrrole, pyridine, pyrimidine, quinoline and triazine; residues of oxygen-containing compounds such as furan and pyran; residues of sulfur-containing compounds such as thiophene; and groups obtained by substituting the above heterocyclic compound residues with substituent groups such as alkyl groups and alkoxy groups of 1 to 30, and preferably 1 to 20 carbon atoms.

Examples of the oxygen-containing groups, the nitrogen-containing groups, the sulfur-containing groups and the phosphorus-containing groups include the groups mentioned above as substituent groups for the hydrocarbon groups.

Examples of the boron-containing groups include the groups mentioned above as substituent groups for the hydrocarbon groups, and alkylboron groups, arylboron groups, boron halide groups and alkylboron halide groups. The alkylboron groups include $(Et)_2B—$, $(iPr)_2B—$, $(iBu)_2B—$, $(Et)_3B$, $(iPr)_3B$ and $(iBu)_3B$. The arylboron groups include $(C_6H_5)_2B—$, $(C_6H_5)_3B$, $(C_6F_5)_3B$ and $(3,5-(CF_3)_2C_6H_3)_3B$. The boron halide groups include $BCl_2—$ and $BCl_3$. The alkylboron halide groups include $(Et)BCl—$, $(iBu)BCl—$ and $(C_6H_5)_2BCl$. In the above groups, the trisubstituted boron is often coordination bonded. Here, Et denotes an ethyl group, iPr an isopropyl group, and iBu an isobutyl group.

Examples of the aluminum-containing groups include alkylaluminum groups, arylaluminum groups, aluminum halide groups and alkylaluminum halide groups. The alkylaluminum groups include $(Et)_2Al—$, $(iPr)_2Al—$, $(iBu)_2Al—$, $(Et)_3Al$, $(iPr)_3Al$ and $(iBu)_3Al$. The arylaluminum groups include $(C_6H_5)_2Al—$. The aluminum halide groups include $AlCl_2—$ and $AlCl_3$. The alkylaluminum halide groups include $(Et)AlCl—$ and $(iBu)AlCl—$. In the above groups, the trisubstituted aluminum is often coordination bonded. Here, Et denotes an ethyl group, iPr an isopropyl group, and iBu an isobutyl group.

Examples of the silicon-containing groups include silyl groups, siloxy groups, hydrocarbon-substituted silyl groups and hydrocarbon-substituted siloxy groups. The hydrocarbon-substituted silyl groups include methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl and dimethyl(pentafluorophenyl)silyl. Of these, methylsilyl, dimethylsilyl, trimethylsilyl, ethylsilyl, diethylsilyl, triethylsilyl, dimethylphenylsilyl and triphenylsilyl are preferred, and trimethylsilyl, triethylsilyl, triphenylsilyl and dimethylphenylsilyl are particularly preferred. The hydrocarbon-substituted siloxy groups include trimethylsiloxy group.

Examples of the germanium-containing groups and the tin-containing groups include groups corresponding to the above silicon-containing groups except that the silicon is replaced by germanium or tin.

Of the nitrogen-containing groups, preferred amide groups include acetamide, N-methylacetamide and N-methylbenzamide; preferred amino groups include dimethylamino, ethylmethylamino and diphenylamino; preferred imide groups include acetimide and benzimide; and preferred imino groups include methylimino, ethylimino, propylimino, butylimino and phenylimino.

Of the sulfur-containing groups, preferred alkylthio groups include methylthio and ethylthio; preferred arylthio groups include phenylthio, methylphenylthio and naphthylthio; preferred thioester groups include acetylthio, benzoylthio, methylthiocarbonyl and phenylthiocarbonyl; preferred sulfonate groups include methyl sulfonate, ethyl sulfonate and phenyl sulfonate; and preferred sulfonamide groups include phenylsulfonamide, N-methylsulfonamide and N-methyl-p-toluenesulfonamide.

Two or more of $R^1$ to $R^6$ may be linked together. Preferably, adjacent groups of $R^1$ to $R^6$ are linked together to form an alicyclic ring, an aromatic ring, or a heterohydrocarbon ring containing heteroatoms such as nitrogen. These rings may have substituent groups.

$R^1$ may be linked to Z, in which case the linkage of $R^1$ with Z may form an aromatic ring, an alicyclic ring, or a heterohydrocarbon ring containing heteroatoms such as nitrogen, and these rings may have substituent groups.

$R^1$ is preferably a methyl group, an ethyl group or an isopropyl group, and is particularly preferably a methyl group.

$R^2$ is preferably a phenyl group, an α-cumyl group, a tert-butyl group or a 1-adamantyl group, and is particularly preferably a 1-adamantyl group.

$R^4$ is preferably a methyl group, a cyclohexyl group, a tert-butyl group or a 1-adamantyl group, and is particularly preferably a methyl group.

In Formula (I), M is a transition metal atom of Group 3 to Group 10 of the periodic table, and n is a valence of M. Preferred examples of M include yttrium, scandium, lanthanum, samarium, titanium, zirconium, hafnium, vanadium, tantalum, chromium, cobalt, iron, nickel and copper. M is more preferably a transition metal atom of Group 4 of the periodic table such as titanium, zirconium or hafnium, and is particularly preferably titanium. Particularly preferably, the letter n is 3 for yttrium, scandium and lanthanum, is 2 for samarium, is 4 for Group 4 transition metal atoms such as titanium, zirconium and hafnium, is 3 to 5 for vanadium and tantalum, is 3 for chromium, and is 2 for cobalt, iron, nickel and copper.

In Formula (I), X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group. The atoms or groups indicated by X may be the same or different from each other, and the groups indicated by X may be linked to each other to form a ring.

Examples of the halogen atoms include fluorine, chlorine, bromine and iodine.

Examples of the hydrocarbon groups include those mentioned for $R^1$ to $R^6$ in Formula (I).

Specific examples include, but are not limited to, alkyl groups such as methyl, ethyl, propyl, butyl, hexyl, octyl, nonyl, dodecyl and eicosyl; cycloalkyl groups of 3 to 30 carbon atoms such as cyclopentyl, cyclohexyl, norbornyl and adamantyl; alkenyl groups such as vinyl, propenyl and cyclohexenyl; arylalkyl groups such as benzyl, phenylethyl and phenylpropyl; and aryl groups such as phenyl, tolyl, dimethylphenyl, trimethylphenyl, ethylphenyl, propylphenyl, biphenyl, naphthyl, methylnaphthyl, anthryl and phenanthryl. Examples of the hydrocarbon groups further include halogenated hydrocarbon groups, specifically hydrocarbon groups of 1 to 30, and preferably 1 to 20 carbon atoms wherein at least one hydrogen is substituted with halogen.

Examples of the heterocyclic compound residues include those mentioned for $R^1$ to $R^6$ in Formula (I).

Examples of the oxygen-containing groups include those mentioned for $R^1$ to $R^6$ in Formula (I). Specific examples include, but are not limited to, hydroxyl group; alkoxy groups such as methoxy, ethoxy, propoxy and butoxy; aryloxy groups such as phenoxy, methylphenoxy, dimethylphenoxy and naphthoxy; arylalkoxy groups such as phenylmethoxy and phenylethoxy; acetoxy groups; and carbonyl groups.

Examples of the sulfur-containing groups include those mentioned for $R^1$ to $R^6$ in Formula (I). Specific examples include, but are not limited to, sulfonate groups such as methyl sulfonate, trifluoromethane sulfonate, phenyl sulfonate, benzyl sulfonate, p-toluene sulfonate, trimethylbenzene sulfonate, triisobutylbenzene sulfonate, p-chlorobenzene sulfonate and pentafluorobenzene sulfonate; sulfinate groups such as methyl sulfinate, phenyl sulfinate, benzyl sulfinate, p-toluene sulfinate, trimethylbenzene sulfinate and pentafluorobenzene sulfinate; alkylthio groups; and arylthio groups.

Examples of the nitrogen-containing groups include those mentioned for $R^1$ to $R^6$ in Formula (I). Specific examples include, but are not limited to, amino groups; alkylamino groups such as methylamino, dimethylamino, diethylamino, dipropylamino, dibutylamino and dicyclohexylamino; and arylamino groups and alkylarylamino groups such as phenylamino, diphenylamino, ditolylamino, dinaphthylamino and methylphenylamino.

Examples of the boron-containing groups include $BR_4$ other than tetraphenyl borate (where R is a hydrogen atom, an alkyl group, an optionally substituted aryl group, or a halogen atom).

Examples of the phosphorus-containing groups include, but are not limited to, trialkylphosphine groups such as trimethylphosphine, tributylphosphine and tricyclohexylphosphine; triarylphosphine groups such as triphenylphosphine and tritolylphosphine; phosphite groups (phosphide groups) such as methyl phosphite, ethyl phosphite and phenyl phosphite; phosphonic acid groups; and phosphinic acid groups.

Examples of the silicon-containing groups include those mentioned for $R^1$ to $R^6$ in Formula (I). Specific examples include hydrocarbon-substituted silyl groups such as phenylsilyl, diphenylsilyl, trimethylsilyl, triethylsilyl, tripropylsilyl, tricyclohexylsilyl, triphenylsilyl, methyldiphenylsilyl, tritolylsilyl and trinaphthylsilyl; hydrocarbon-substituted silyl ether groups such as trimethylsilyl ether; silicon-substituted alkyl groups such as trimethylsilylmethyl; and silicon-substituted aryl groups such as trimethylsilylphenyl.

Examples of the germanium-containing groups include those mentioned for $R^1$ to $R^6$ in Formula (I). Specific examples include groups corresponding to the above silicon-containing groups except that the silicon is replaced by germanium.

Examples of the tin-containing groups include those mentioned for $R^1$ to $R^6$ in Formula (I). Specific examples include groups corresponding to the above silicon-containing groups except that the silicon is replaced by tin.

Examples of the halogen-containing groups include, but are not limited to, fluorine-containing groups such as $PF_6$ and $BF_4$; chlorine-containing groups such as $ClO_4$ and $SbCl_6$; and iodine-containing groups such as $IO_4$.

Examples of the aluminum-containing groups include, but are not limited to, $AlR_4$ (where R is a hydrogen atom, an alkyl group, an optionally substituted aryl group, or a halogen atom).

Of the above atoms and groups indicated by X, the halogen atoms and the alkyl groups are preferred, and chlorine, bromine and methyl are more preferred.

In Formula (I), Y is an oxygen atom, a nitrogen atom, a phosphorus atom or a sulfur atom, and constitutes an ether structure, a ketone structure, an amine structure or an imine structure.

In Formula (I), Z is a hydrocarbon group or a heterocyclic compound residue that may have a substituent group, and the minimum number of bonds linking Y with N is in the range of 4 to 6.

By limiting the minimum number of bonds linking Y with N in the range of 4 to 6, the olefin oligomerization catalyst containing the transition metal complex compound [A] catalyzes the oligomerization of ethylene to afford 1-hexene with high selectivity. Preferably, the minimum number of bonds linking Y with N is 5 or 6, in which case the selectivity for 1-hexene is further increased.

If the minimum number of bonds between Y and N is 3 or less, the distance between Y and N is not sufficient and the catalyst works to polymerize ethylene, that is, the catalyst is an olefin polymerization catalyst similar to compounds described in WO 2001/44324, Organometallics, 2004, Vol. 23, pp. 1684-1688, and Organometallics, 2006, Vol. 25, pp. 3259-3266. Consequently, oligomers such as 1-hexene are not produced as expected.

If the minimum number of bonds between Y and N is 7 or more, Y cannot be coordinated to the metal atom M, and the catalyst works to polymerize ethylene, that is, the catalyst is an olefin polymerization catalyst similar to compounds without Y as described in Dalton Transaction, 2005, pp. 561-571. Consequently, oligomers such as 1-hexene are not produced as expected.

The minimum number of bonds linking Y with N is counted as shown in (A) and (B) below, in which the minimum numbers are 4 and 5, respectively.

[Chem. 6]

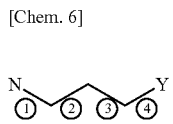
(A)

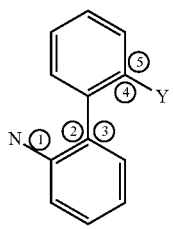
(B)

The letter Z denotes a group linking N and Y. Preferably, Y, N and Z form a structure represented by Formula (II):

[Chem. 7]

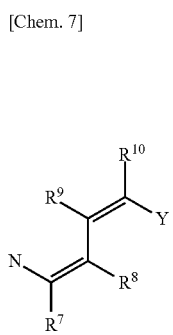
(II)

wherein Y is an oxygen atom, a nitrogen atom, a phosphorus atom or a sulfur atom; and $R^7$ to $R^{10}$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and when $R^7$ to $R^{10}$ are hydrocarbon groups, $R^7$ and $R^8$ may be linked to each other to form a ring and $R^9$ and $R^{10}$ may be linked to each other to form a ring.

Specific examples of $R^7$ to $R^{10}$ include those described for $R^1$ to $R^6$ in Formula (I).

Specific examples of the structures formed by Y, N and Z include those represented by Formulae (C) to (H) below but are not limited thereto. In the structures of Formulae (C) to (H), hydrogen atoms may be substituted with the groups mentioned above as substituent groups for $R^1$ to $R^6$. In some of the structures of Formulae (C) to (H), $R^1$ is linked to Z.

In the structures illustrated below, the wavy lines adjacent to a carbon-carbon double bond indicate a cis-isomer or a trans-isomer.

[Chem. 8]

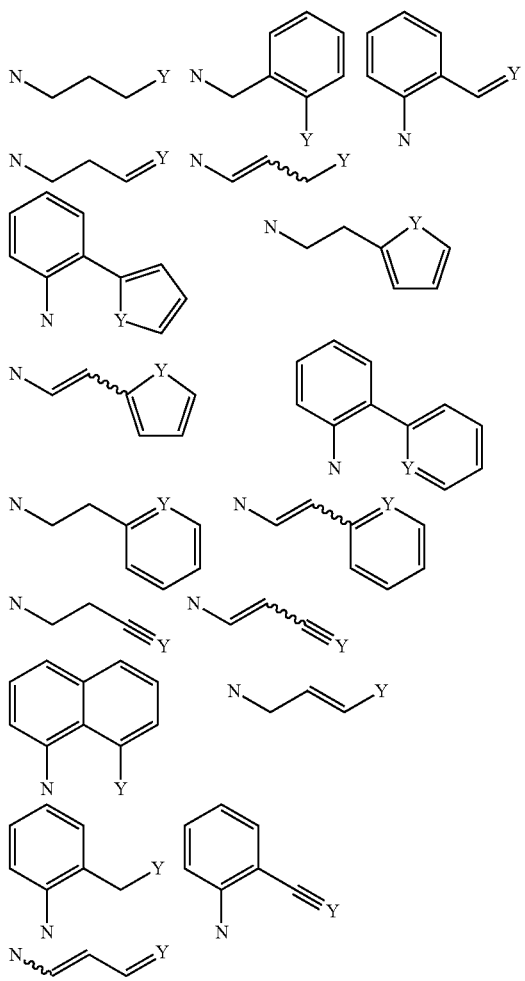
(C)

[Chem. 9]

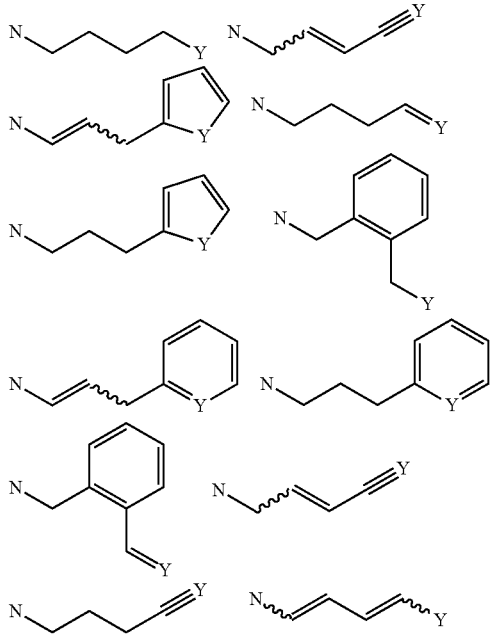
(D)

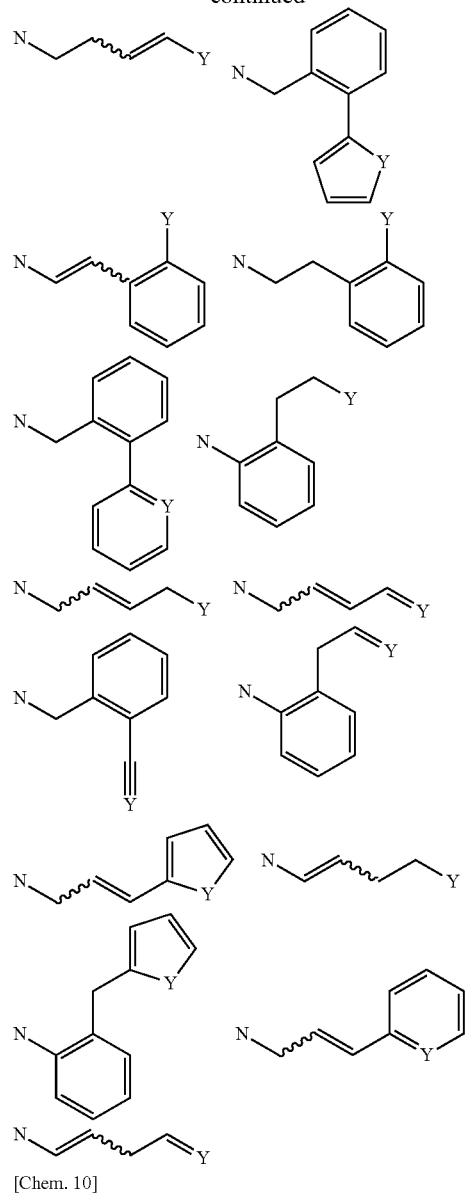
[Chem. 10]
(E)
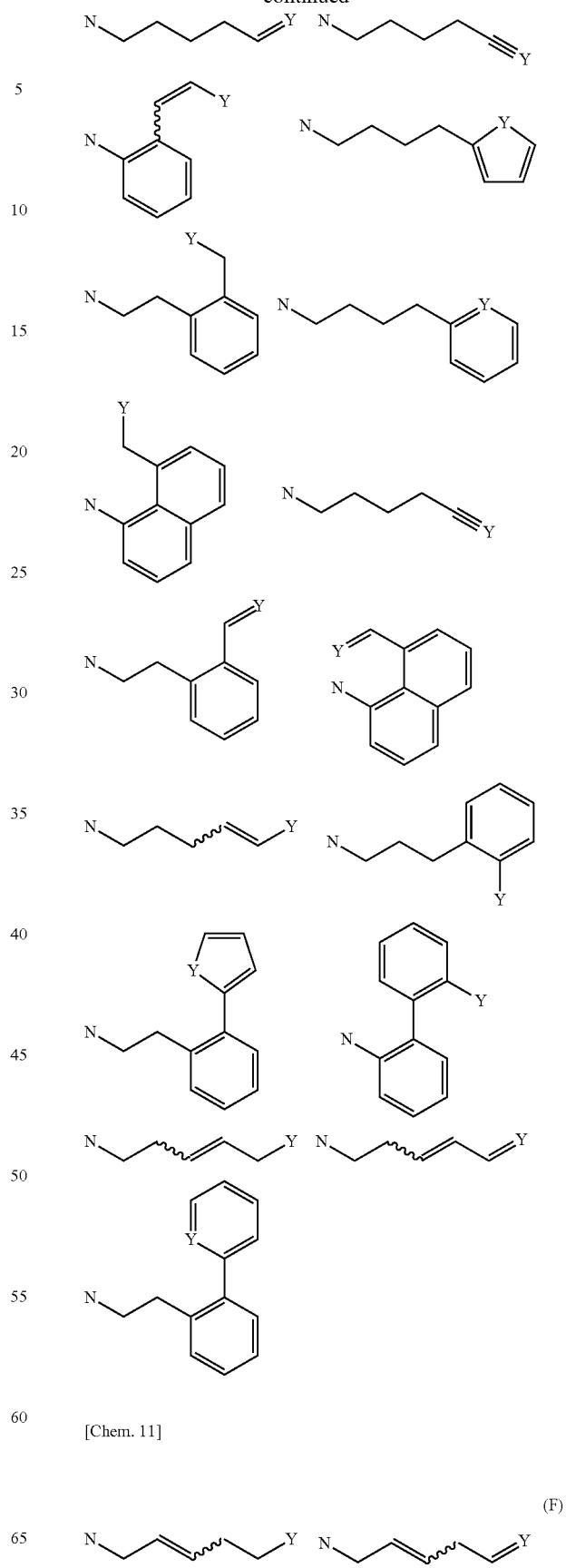
[Chem. 11]
(F)

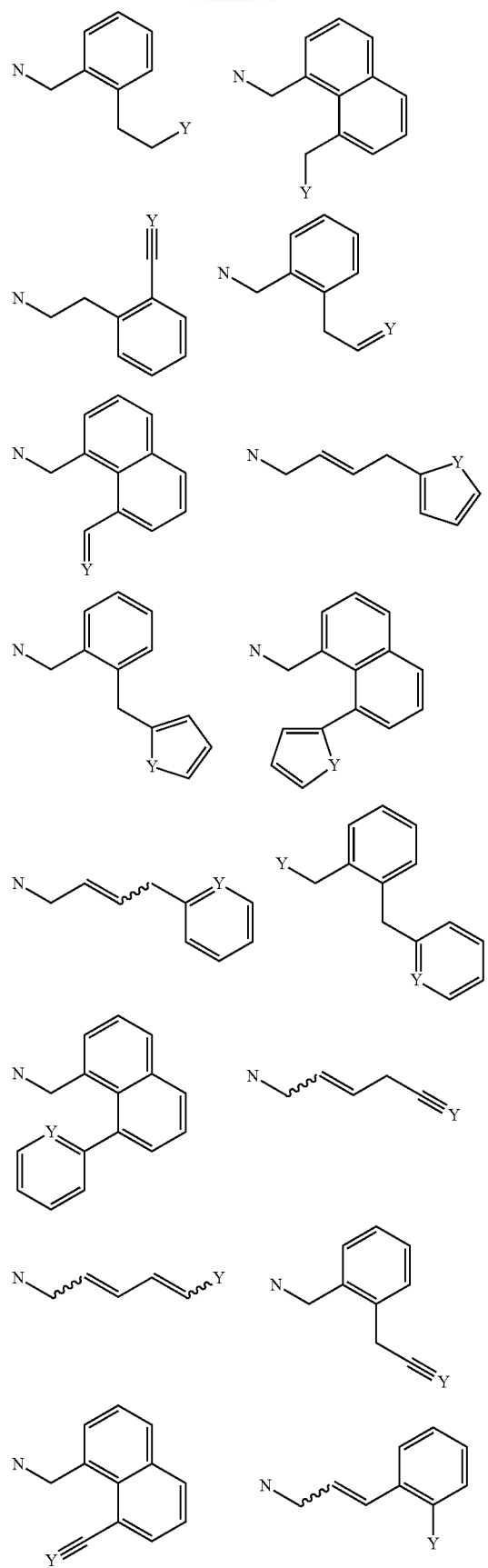
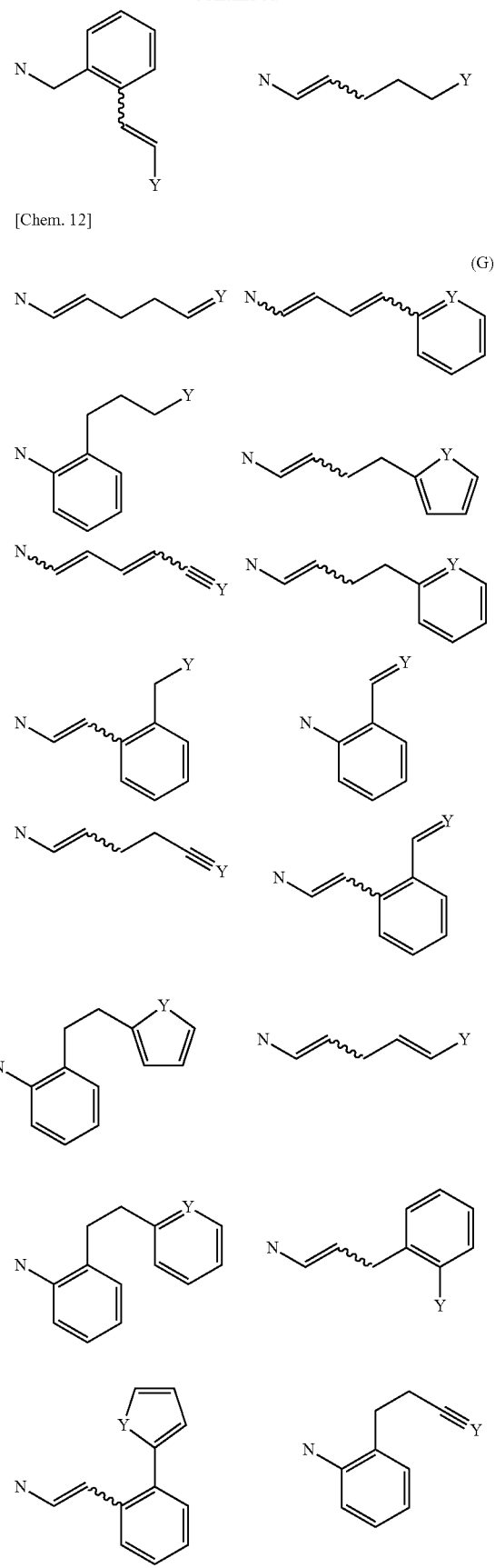
[Chem. 12]

-continued

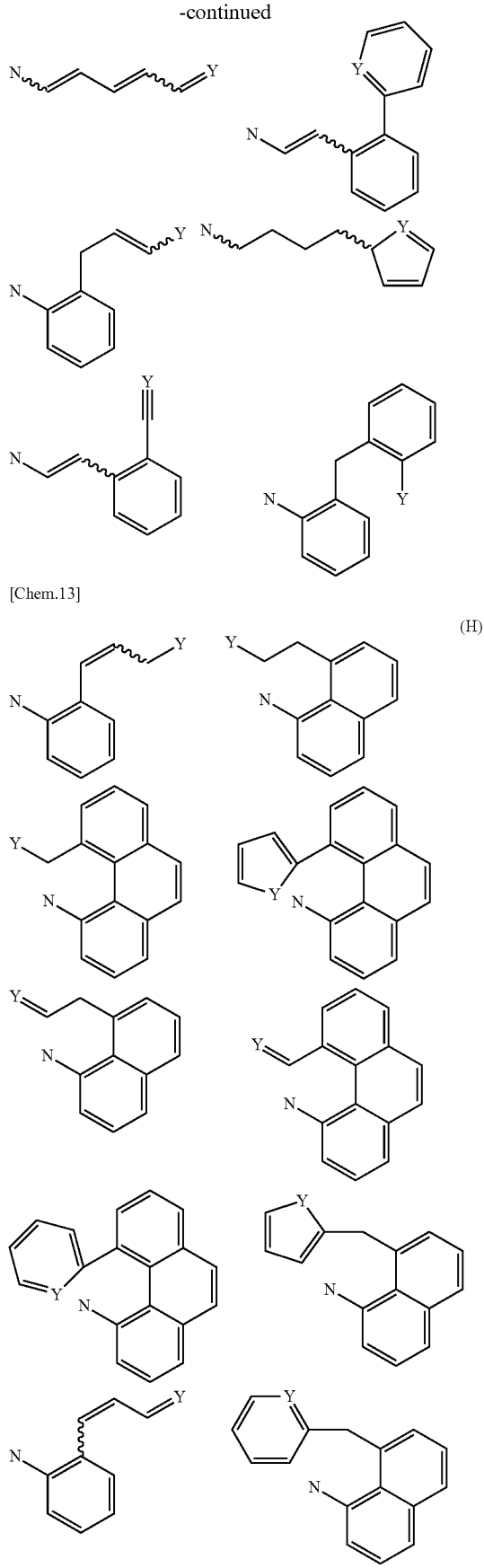
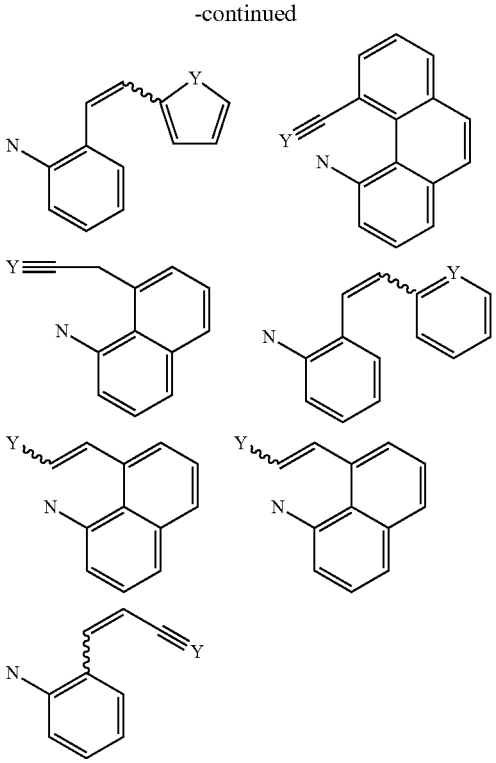

[Chem.13]

(H)

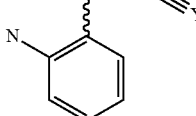

In Formula (I), the bond between Y and Z may be a double bond or a triple bond, and the bond between Y and R¹ may be a double bond or a triple bond. In Formula (I), the dotted lines each denote a coordination bond.

The transition metal complex compounds [A] in the second embodiment are represented by Formula (I') below:

[Chem. 14]

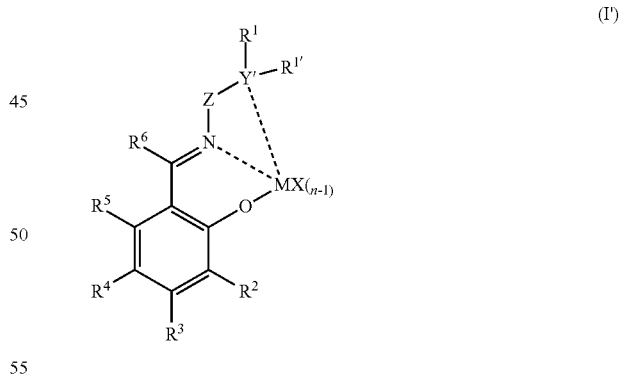

(I')

In Formula (I'), $R^1$ to $R^6$ and $R^{1'}$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group. Two or more of $R^{1'}$ and $R^1$ to $R^6$ may be linked to each other, and $R^1$ may be linked to Z. Examples of $R^1$ to $R^6$ and $R^{1'}$ in Formula (I') include those mentioned for $R^1$ to $R^6$ in Formula (I).

In Formula (I'), M is a transition metal atom of Group 3 to Group 10 of the periodic table, and n is a valence of M. Examples of M and n in Formula (I') include those mentioned for M and n in Formula (I).

In Formula (I'), X is a hydrogen atom, a halogen atom, a hydrocarbon group, an oxygen-containing group, a sulfur-containing group, a nitrogen-containing group, boron-containing group, an aluminum-containing group, a phosphorus-containing group, a halogen-containing group, a heterocyclic compound residue, a silicon-containing group, a germanium-containing group or a tin-containing group. The atoms or groups indicated by X may be the same or different from each other, and the groups indicated by X may be linked to each other to form a ring. Examples of X in Formula (I') include those mentioned for X in Formula (I).

In Formula (I'), Y' is a nitrogen atom or a phosphorus atom.

In Formula (I'), Z is a hydrocarbon group or a heterocyclic compound residue that may have a substituent group, and the minimum number of bonds linking Y' with N is in the range of 4 to 6.

By limiting the minimum number of bonds linking Y' with N in the range of 4 to 6, the olefin oligomerization catalyst containing the transition metal complex compound [A] catalyzes the oligomerization of ethylene to afford 1-hexene with high selectivity. Preferably, the minimum number of bonds linking Y' with N is 5 or 6, in which case the selectivity for 1-hexene is further increased.

Specific examples of the structures formed by Y', N and Z include those represented by Formulae (I) to (K) below but are not limited thereto. In the structures of Formulae (I) to (K), hydrogen atoms may be substituted with the groups mentioned above as substituent groups for $R^1$ to $R^6$ in Formula (I). In some of the structures of Formulae (I) to (K), $R^1$ is linked to Z.

In the structures illustrated below, the wavy lines adjacent to a carbon-carbon double bond indicate a cis-isomer or a trans-isomer.

[Chem. 15]

(I)

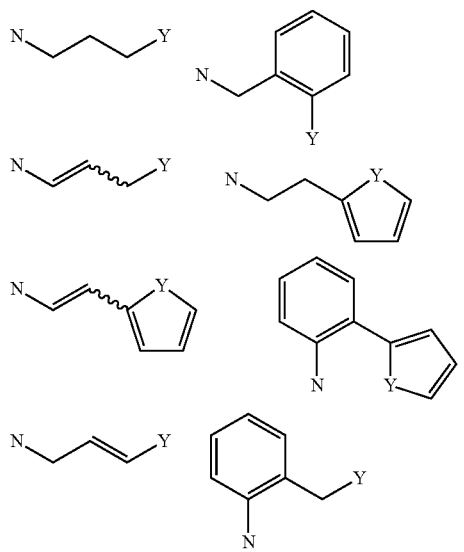

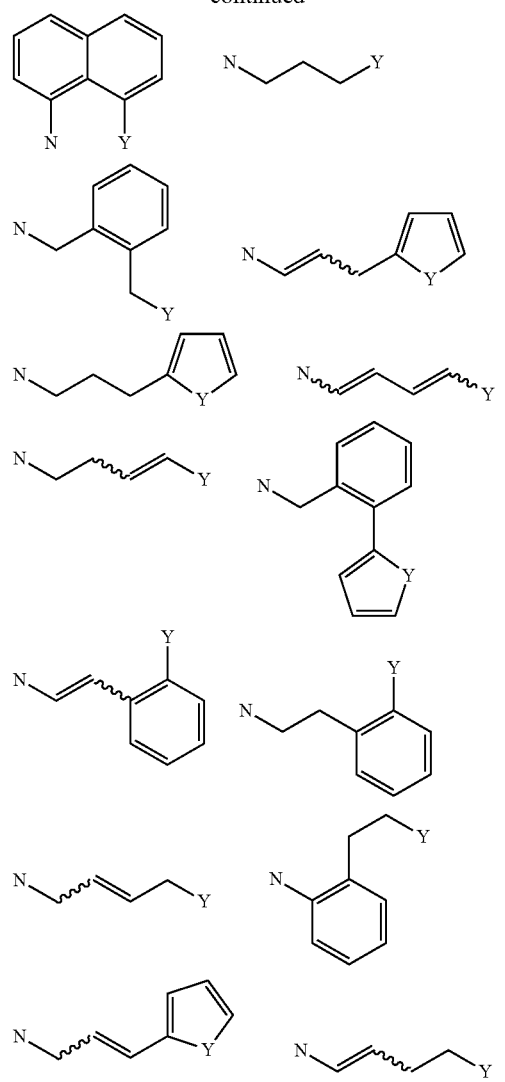

[Chem. 16]

(J)

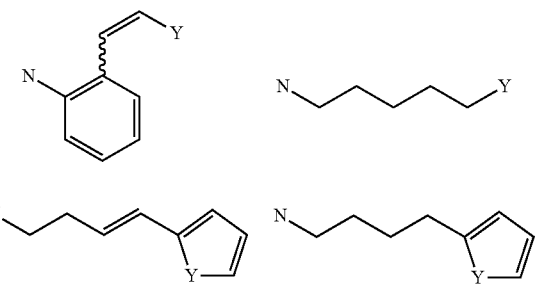

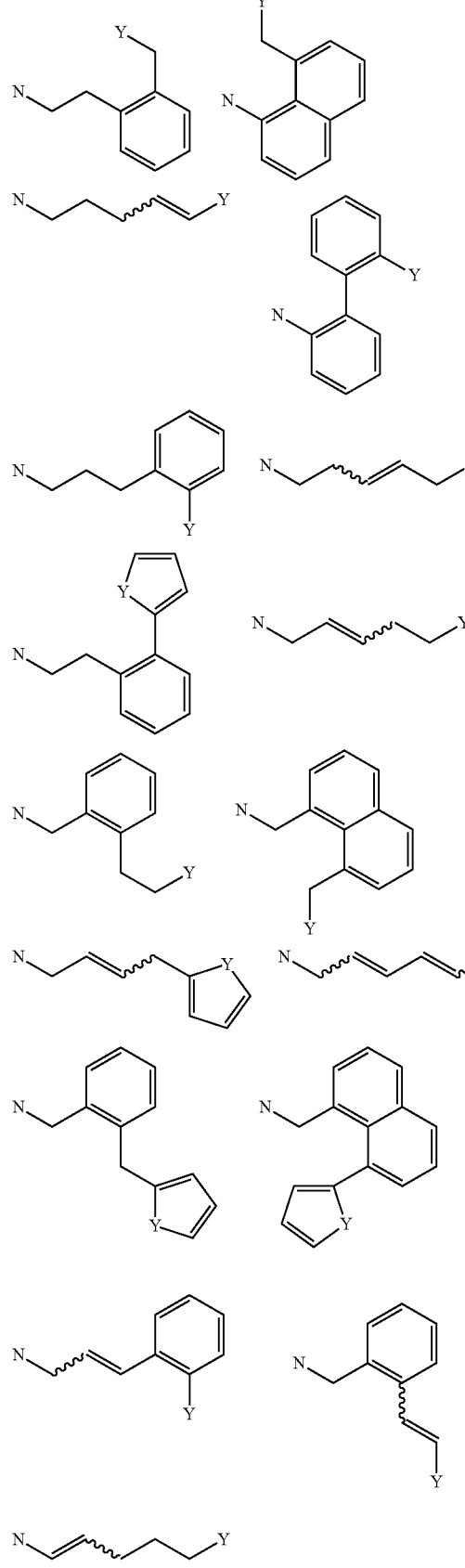
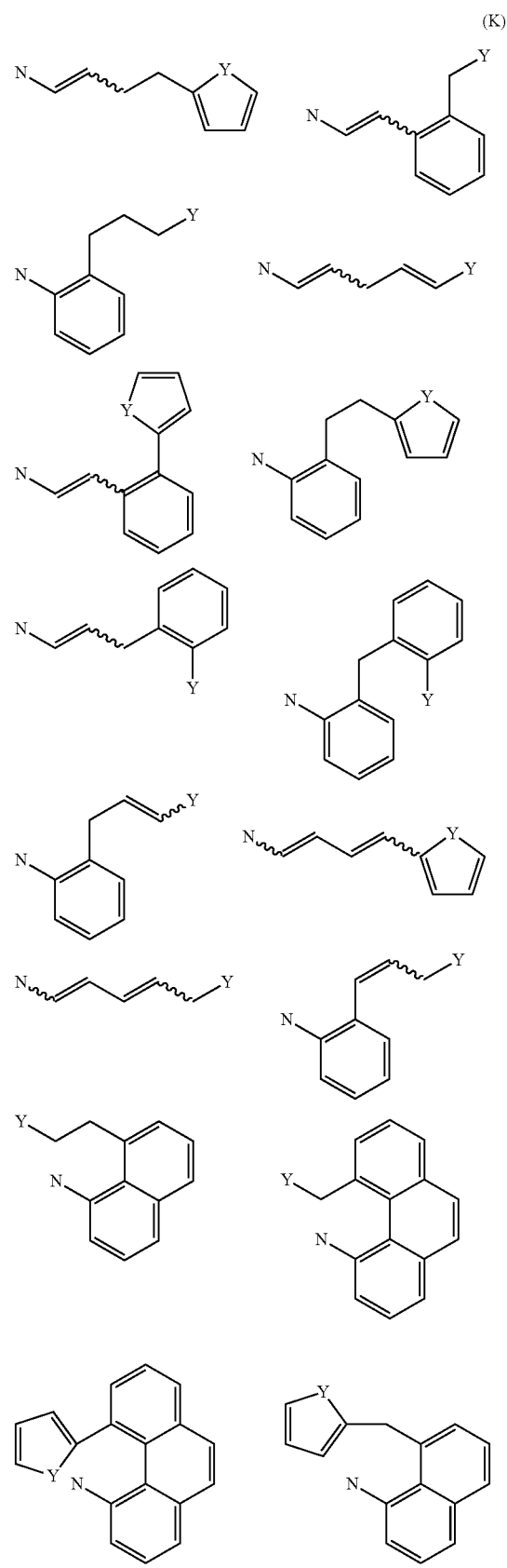
[Chem. 17]
(K)

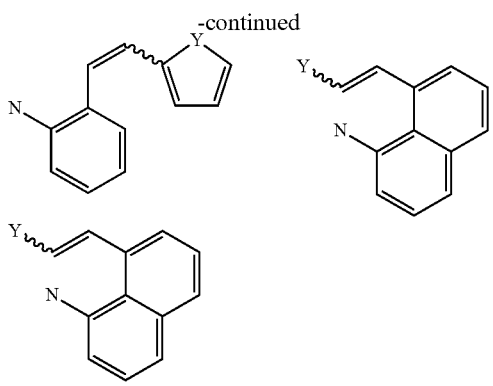

In Formula (I'), the dotted lines each denote a coordination bond.

The transition metal complex compounds [A] of Formula (I) and Formula (I') may be synthesized according to a method described in Journal of Organometallic Chemistry, 2003, Vol. 678, pp. 134-141.

The reaction product by the method described in the above literature is a mixture but may be used directly as an olefin oligomerization catalyst without purification. Preferably, the product is used after purified by recrystallization or the like.

In the invention, the transition metal complex compounds of Formula (I) and the transition metal complex compounds of Formula (I') may be collectively referred to as the transition metal complex compounds [A].

In addition to the transition metal complex compound [A], the olefin oligomerization catalyst according to the present invention usually contains at least one compound [B] selected from the group consisting of (b-1) an organometallic compound, (b-2) an organoaluminum oxy-compound and (b-3) a compound which reacts with the transition metal complex compound [A] to form an ion pair. The catalyst may further contain a carrier [C] to support at least one compound selected from [A] and [B].

Hereinbelow, the organometallic compounds (b-1), organoaluminum oxy-compounds (b-2), and compounds (b-3) which react with the transition metal complex compound [A] to form an ion pair will be described.

[Organometallic Compounds (b-1)]

Examples of the organometallic compounds (b-1) that are optionally used in the invention include organometallic compounds containing metals of Group 1, Group 2, Group 12 and Group 13 of the periodic table. Specific examples include compounds (b-1a), (b-1b) and (b-1c) described below. In the invention, the organometallic compounds (b-1) do not include the organoaluminum oxy-compounds (b-2).

(b-1a) Organoaluminum compounds represented by the following formula:

wherein $R^a$ and $R^b$, which may be the same or different, are each a hydrocarbon group of 1 to 15, and preferably 1 to 4 carbon atoms; X is a halogen atom; $0<m\leqq3$, $0\leqq n<3$, $0\leqq p<3$, $0\leqq q<3$ and $m+n+p+q=3$.

(b-1b) Alkyl complex compounds containing a Group 1 metal of the periodic table and aluminum and represented by the following formula:

wherein $M^2$ is Li, Na or K; and $R^a$ is a hydrocarbon group of 1 to 15, and preferably 1 to 4 carbon atoms.

(b-1c) Dialkyl compounds containing a Group 2 or Group 12 metal of the periodic table and represented by the following formula:

wherein $R^a$ and $R^b$, which may be the same or different, are each a hydrocarbon group of 1 to 15, and preferably 1 to 4 carbon atoms; and $M^3$ is Mg, Zn or Cd.

Examples of the organoaluminum compounds (b-1a) include:

organoaluminum compounds represented by the following formula:

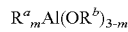

wherein $R^a$ and $R^b$, which may be the same or different, are each a hydrocarbon group of 1 to 15, and preferably 1 to 4 carbon atoms, and m is preferably $1.5\leqq m\leqq3$;

organoaluminum compounds represented by the following formula:

wherein $R^a$ is a hydrocarbon group of 1 to 15, and preferably 1 to 4 carbon atoms, X is a halogen atom, and m is preferably $0<m<3$;

organoaluminum compounds represented by the following formula:

wherein $R^a$ is a hydrocarbon group of 1 to 15, and preferably 1 to 4 carbon atoms, and m is preferably $2\leqq m<3$; and organoaluminum compounds represented by the following formula:

wherein $R^a$ and $R^b$, which may be the same or different, are each a hydrocarbon group of 1 to 15, and preferably 1 to 4 carbon atoms, X is a halogen atom, $0<m\leqq3$, $0\leqq n<3$, $0\leqq q<3$ and $m+n+q=3$.

Specific examples of the organoaluminum compounds (b-1a) include:

tri(n-alkyl)aluminums such as trimethylaluminum, triethylaluminum, tri(n-butyl)aluminum, tripropylaluminum, tripentylaluminum, trihexylaluminum, trioctylaluminum and tridecylaluminum;

branched-chain trialkylaluminums such as triisopropylaluminum, triisobutylaluminum, tri(sec-butyl)aluminum, tri(tert-butyl)aluminum, tri(2-methylbutyl)aluminum, tri(3-methylbutyl)aluminum, tri(2-methylpentyl)aluminum, tri(3-methylpentyl)aluminum, tri(4-methylpentyl)aluminum, tri(2-methylhexyl)aluminum, tri(3-methylhexyl)aluminum and tri(2-ethylhexyl)aluminum;

tricycloalkylaluminums such as tricyclohexylaluminum and tricyclooctylaluminum;

triarylaluminums such as triphenylaluminum and tritolylaluminum;

dialkylaluminum hydrides such as diethylaluminum hydride and diisobutylaluminum hydride;

alkenylaluminums such as those represented by the formula $(i-C_4H_9)_xAl_y(C_5H_{10})_z$ (wherein x, y and z are each a positive number, $z\geqq2x$, and $i-C_4H_9$ is an isobutyl group) with examples including isoprenylaluminum;

alkylaluminum alkoxides such as isobutylaluminum methoxide, isobutylaluminum ethoxide and isobutylaluminum isopropoxide;

dialkylaluminum alkoxides such as dimethylaluminum methoxide, diethylaluminum ethoxide and dibutylaluminum butoxide;

alkylaluminum sesquialkoxides such as ethylaluminum sesquiethoxide and butylaluminum sesquibutoxide;

partially alkoxylated alkylaluminums such as those having an average composition represented by $R^a{}_{2.5}Al(OR^b)_{0.5}$ (wherein $R^a$ and $R^b$, which may be the same or different, are each a hydrocarbon group of 1 to 15, and preferably 1 to 4 carbon atoms);

dialkylaluminum aryloxides such as diethylaluminum phenoxide, diethylaluminum(2,6-di-t-butyl-4-methylphenoxide), ethylaluminumbis(2,6-di-t-butyl-4-methylphenoxide), diisobutylalumium(2,6-di-t-butyl-4-methylphenoxide) and isobutylaluminumbis(2,6-di-t-butyl-4-methylphenoxide);

dialkylaluminum halides such as dimethylaluminum chloride, diethylaluminum chloride, dibutylaluminum chloride, diethylaluminum bromide and diisobutylaluminum chloride;

alkylaluminum sesquihalides such as ethylaluminum sesquichloride, butylaluminum sesquichloride and ethylaluminum sesquibromide;

partially halogenated alkylaluminums such as alkylaluminum dihalides including ethylaluminum dichloride, propylaluminum dichloride and butylaluminum dibromide;

dialkylaluminum hydrides such as diethylaluminum hydride and dibutylaluminum hydride;

partially hydrogenated alkylaluminums such as alkylaluminum dihydrides including ethylaluminum dihydride and propylaluminum dihydride; and partially alkoxylated and halogenated alkylaluminums such as ethylaluminum ethoxychloride, butylaluminum butoxychloride and ethylaluminum ethoxybromide.

Compounds analogous to the organoaluminum compounds (b-1a) are also employable. Examples of such compounds include organoaluminum compounds wherein two or more aluminum compounds are bonded via a nitrogen atom, such as $(C_2H_5)_2AlN(C_2H_5)Al(C_2H_5)_2$.

Examples of the compounds (b-1b) include $LiAl(C_2H_5)_4$ and $LiAl(C_7H_{15})_4$.

Examples of the compounds (b-1c) include dimethylmagnesium, diethylmagnesium, dibutylmagnesium and butylethylmagnesium.

Examples of the organometallic compounds (b-1) other than the compounds (b-1a) to (b-1c) include methyllithium, ethyllithium, propyllithium, butyllithium, methylmagnesium bromide, methylmagnesium chloride, ethylmagnesium bromide, ethylmagnesium chloride, propylmagnesium bromide, propylmagnesium chloride, butylmagnesium bromide and butylmagnesium chloride.

Combinations of compounds capable of forming the above organoaluminum compounds in the oligomerization system are also employable, with examples including a combination of aluminum halide and alkyllithium and a combination of aluminum halide and alkylmagnesium.

Of the organometallic compounds (b-1), the organoaluminum compounds are preferable. The organometallic compounds (b-1) may be used singly, or two or more kinds may be used in combination.

[Organoaluminum Oxy-Compounds (b-2)]

The organoaluminum oxy-compounds (b-2) that are optionally used in the invention may be conventional aluminoxanes or benzene-insoluble organoaluminum oxy-compounds as described in JP-A-H02-78687.

For example, conventional aluminoxane may be prepared by the following processes, and is generally obtained as a solution in a hydrocarbon solvent.

(1) An organoaluminum compound such as trialkylaluminum is added to a hydrocarbon medium suspension of a compound containing water of adsorption or a salt containing water of crystallization, e.g., magnesium chloride hydrate, copper sulfate hydrate, aluminum sulfate hydrate, nickel sulfate hydrate or cerous chloride hydrate, to allow the organoaluminum compound to react with the water of adsorption or the water of crystallization.

(2) Water, ice or water vapor is allowed to directly act on an organoaluminum compound such as trialkylaluminum in a medium such as benzene, toluene, ethyl ether or tetrahydrofuran.

(3) An organotin oxide such as dimethyltin oxide or dibutyltin oxide is allowed to react with an organoaluminum compound such as trialkylaluminum in a medium such as decane, benzene or toluene.

The aluminoxane may contain a small amount of an organometallic component. Further, the solvent or the unreacted organoaluminum compound may be distilled off from the solution of aluminoxane, and the distillate may be redissolved in a solvent or suspended in a poor solvent for the aluminoxane.

Examples of the organoaluminum compounds used in the preparation of aluminoxanes include the organoaluminum compounds described above for the organoaluminum compounds (b-1a).

Of the organoaluminum compounds, the trialkylaluminums and tricycloalkylaluminums are preferable, and trimethylaluminum is particularly preferable.

The organoaluminum compounds may be used singly, or two or more kinds may be used in combination.

Examples of the solvents used in the preparation of aluminoxanes include aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosine and light oil; and halides such as chlorides and bromides of these aromatic, aliphatic and alicyclic hydrocarbons. Ethers such as ethyl ether and tetrahydrofuran are also employable. Of the solvents, the aromatic hydrocarbons and the aliphatic hydrocarbons are particularly preferable.

The benzene-insoluble organoaluminum oxy-compound preferably contains an Al component which is soluble in benzene at 60° C., in an amount of not more than 10%, preferably not more than 5%, and particularly preferably not more than 2% in terms of Al atom. That is, the benzene-insoluble organoaluminum oxy-compound is preferably insoluble or hardly soluble in benzene.

Examples of the organoaluminum oxy-compounds for use in the invention further include boron-containing organoaluminum oxy-compounds represented by Formula (i):

[Chem. 18]

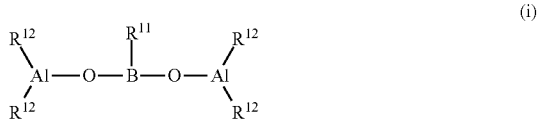

(i)

In the formula, $R^{11}$ is a hydrocarbon group of 1 to 10 carbon atoms; and the plurality of $R^{12}$, which may be the same or different, are each a hydrogen atom, a halogen atom or a hydrocarbon group of 1 to 10 carbon atoms.

The boron-containing organoaluminum oxy-compounds represented by Formula (i) may be prepared by allowing an alkylboronic acid represented by Formula (ii):

$$R^{11}-B(OH)_2 \quad (ii)$$

wherein $R^{11}$ is the same as described above, to react with an organoaluminum compound in an inert solvent at a temperature of −80° C. to room temperature for 1 minute to 24 hours under an inert gas atmosphere.

Examples of the alkylboronic acids represented by Formula (ii) include methylboronic acid, ethylboronic acid, isopropylboronic acid, n-propylboronic acid, n-butylboronic acid, isobutylboronic acid, n-hexylboronic acid, cyclohexylboronic acid, phenylboronic acid, 3,5-difluorophenylboronic acid, pentafluorophenylboronic acid and 3,5-bis(trifluoromethyl)phenylboronic acid. Of these, methylboronic acid, n-butylboronic acid, isobutylboronic acid, 3,5-difluorophenylboronic acid and pentafluorophenylboronic acid are preferable.

These alkylboronic acids may be used singly, or two or more kinds may be used in combination.

Examples of the organoaluminum compounds to be reacted with the alkylboronic acids include the organoaluminum compounds described above for the organoaluminum compounds (b-1a). Of these, the trialkylaluminums and tricycloalkylaluminums are preferable, and trimethylaluminum, triethylaluminum and triisobutylaluminum are particularly preferable. The organoaluminum compounds may be used singly, or two or more kinds may be used in combination.

The organoaluminum oxy-compounds (b-2) mentioned above may be used singly, or two or more kinds may be used in combination.

[Ionizing Ionic Compounds (b-3)]

The compounds (b-3) that are optionally used in the invention are compounds which react with the transition metal compound (A) to form an ion pair. Any compounds capable of reacting with the transition metal compound (A) to form an ion pair may be used in the invention.

Examples of such compounds include Lewis acids, ionic compounds, borane compounds and carborane compounds as described in JP-A-H01-501950, JP-A-H01-502036, JP-A-H03-179005, JP-A-H03-179006, JP-A-H03-207703, JP-A-H03-207704, and U.S. Pat. No. 5,321,106. Heteropoly compounds and isopoly compounds may also be employed.

The Lewis acids include compounds represented by $BR_3$ (R is a fluorine atom or a phenyl group which may have a substituent group such as fluorine, methyl or trifluoromethyl). Specific examples include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris(3,5-dimethylphenyl)boron.

The ionic compounds include compounds represented by Formula (III):

[Chem. 19]

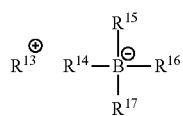

(III)

In the above formula, $R^{13+}$ is $H^+$, carbonium cation, oxonium cation, ammonium cation, phosphonium cation, cycloheptyltrienyl cation, or ferrocenium cation having a transition metal.

$R^{14}$ to $R^{17}$, which may be the same or different, are each an organic group, and preferably an aryl group or a substituted aryl group.

Examples of the carbonium cations include tri-substituted carbonium cations such as triphenylcarbonium cation, tri(methylphenyl)carbonium cation and tri(dimethylphenyl)carbonium cation.

Examples of the ammonium cations include trialkylammonium cations such as trimethylammonium cation, triethylammonium cation, tri(n-propyl)ammonium cation and tri(n-butyl)ammonium cation; N,N-dialkylanilinium cations such as N,N-dimethylanilinium cation, N,N-diethylanilinium cation and N,N,2,4,6-pentamethylanilinium cation; and dialkylammonium cations such as di(isopropyl)ammonium cation and dicyclohexylammonium cation.

Examples of the phosphonium cations include triarylphosphonium cations such as triphenylphosphonium cation, tri(methylphenyl)phosphonium cation and tri(dimethylphenyl)phosphonium cation.

$R^{13+}$ is preferably carbonium cation or ammonium cation, and particularly preferably triphenylcarbonium cation, N,N-dimethylanilinium cation or N,N-diethylanilinium cation.

Examples of the ionic compounds further include trialkyl-substituted ammonium salts, N,N-dialkylanilinium salts, dialkylammonium salts and triarylphosphonium salts.

Examples of the trialkyl-substituted ammonium salts include triethylammonium tetraphenylborate, tri(n-propyl)ammonium tetraphenylborate, tri(n-butyl)ammonium tetraphenylborate, trimethylammonium tetra(p-tolyl)borate, trimethylammonium tetra(o-tolyl)borate, tri(n-butyl)ammonium tetra(pentafluorophenyl)borate, tri(n-propyl)ammonium tetra(o,p-dimethylphenyl)borate, tri(n-butyl)ammonium tetra(m,m-dimethylphenyl)borate, tri(n-butyl)ammonium tetra(p-trifluoromethylphenyl)borate, tri(n-butyl)ammonium tetra(3,5-ditrifluoromethylphenyl) borate and tri(n-butyl)ammonium tetra(o-tolyl)borate.

Examples of the N,N-dialkylanilinium salts include N,N-dimethylanilinium tetraphenylborate, N,N-diethylanilinium tetraphenylborate and N,N,2,4,6-pentamethylanilinium tetraphenylborate.

Examples of the dialkylammonium salts include di(n-propyl)ammonium tetra(pentafluorophenyl)borate and dicyclohexylammonium tetraphenylborate.

Examples of the ionic compounds further include triphenylcarbenium tetrakis(pentafluorophenyl)borate, N,N-dimethylanilinium tetrakis(pentafluorophenyl)borate, ferrocenium tetra(pentafluorophenyl)borate, triphenylcarbenium pentaphenylcyclopentadienyl complex, N,N-diethylanilinium pentaphenylcyclopentadienyl complex, and boron compounds represented by Formula (IV) or (V).

[Chem. 20]

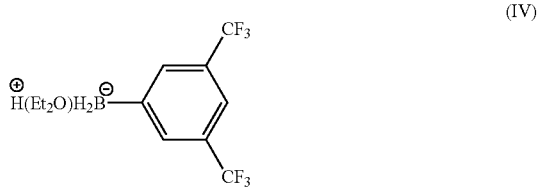

(IV)

In the formula, Et denotes an ethyl group.

[Chem. 21]

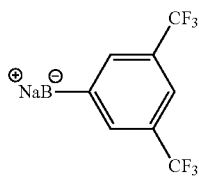

(V)

Examples of the borane compounds include: decaborane (14);

salts of anions such as bis[tri(n-butyl)ammonium]nonaborate, bis[tri(n-butyl)ammonium]decaborate, bis[tri(n-butyl)ammonium]undecaborate, bis[tri(n-butyl)ammonium]dodecaborate, bis[tri(n-butyl)ammonium]decachlorodecaborate and bis[tri(n-butyl)ammonium]dodecachlorododecaborate; and salts of metal cations and borane anions such as tri(n-butyl)ammonium bis(dodecahydridododecaborate)cobaltate(III) and bis[tri(n-butyl)ammonium]bis(dodecahydridododecaborate)nickelate(III).

Examples of the carborane compounds include:

salts of anions such as 4-carbanonaborane (14), 1,3-dicarbanonaborane (13), 6,9-dicarbadecaborane (14), dodecahydrido-1-phenyl-1,3-dicarbanonaborane, dodecahydrido-1-methyl-1,3-dicarbanonaborane, undecahydrido-1,3-dimethyl-1,3-dicarbanonaborane, 7,8-dicarbaundecaborane (13), 2,7-dicarbaundecaborane (13), undecahydrido-7,8-dimethyl-7,8-dicarbaundecaborane, dodecahydrido-11-methyl-2,7-dicarbaundecaborane, tri(n-butyl)ammonium-1-carbadecaborate, tri(n-butyl)ammonium-1-carbaundecaborate, tri(n-butyl)ammonium-1-carbadodecaborate, tri(n-butyl)ammonium-1-trimethylsilyl-1-carbadecaborate, tri(n-butyl)ammoniumbromo-1-carbadodecaborate, tri(n-butyl)ammonium-6-carbadecaborate (14), tri(n-butyl)ammonium-6-carbadecaborate (12), tri(n-butyl)ammonium-7-carbaundecaborate (13), tri(n-butyl)ammonium-7,8-dicarbaundecaborate (12), tri(n-butyl)ammonium-2,9-dicarbaundecaborate (12), tri(n-butyl)ammonium dodecahydrido-8-methyl-7,9-dicarbaundecaborate, tri(n-butyl)ammonium undecahydrido-8-ethyl-7,9-dicarbaundecaborate, tri(n-butyl)ammonium undecahydrido-8-butyl-7,9-dicarbaundecaborate, tri(n-butyl)ammonium undecahydrido-8-allyl-7,9-dicarbaundecaborate, tri(n-butyl)ammonium undecahydrido-9-trimethylsilyl-7,8-dicarbaundecaborate and tri(n-butyl)ammonium undecahydrido-4,6-dibromo-7-carbaundecaborate; and salts of metal cations and carborane anions such as tri(n-butyl)ammonium bis(nonahydrido-1,3-dicarbanonaborate)cobaltate(III), tri(n-butyl)ammonium bis(undecahydrido-7,8-dicarbaundecaborate)ferrate(III), tri(n-butyl)ammonium bis(undecahydrido-7,8-dicarbaundecaborate)cobaltate(III), tri(n-butyl)ammonium bis(undecahydrido-7,8-dicarbaundecaborate)nickelate(III), tri(n-butyl)ammonium bis(undecahydrido-7,8-dicarbaundecaborate)cuprate(III), tri(n-butyl)ammonium bis(undecahydrido-7,8-dicarbaundecaborate)aurate(III), tri(n-butyl)ammonium bis(nonahydrido-7,8-dimethyl-7,8-dicarbaundecaborate)ferrate(III), tri(n-butyl)ammonium bis(nonahydrido-7,8-dimethyl-7,8-dicarbaundecaborate)chromate(III), tri(n-butyl)ammonium bis(tribromooctahydrido-7,8-dicarbaundecaborate)cobaltate(III), tris[tri(n-butyl)ammonium]bis(undecahydrido-7-carbaundecaborate)chromate(III), bis[tri(n-butyl)ammonium]bis(undecahydrido-7-carbaundecaborate)manganate(IV), bis[tri(n-butyl)ammonium]bis(undecahydrido-7-carbaundecaborate) cobaltate (III) and bis[tri(n-butyl)ammonium]bis(undecahydrido-7-carbaundecaborate)nickelate(IV).

The heteropoly compounds contain an atom selected from silicon, phosphorus, titanium, germanium, arsenic and tin, and one or more atoms selected from vanadium, niobium, molybdenum and tungsten. Examples of such compounds include, although not limited thereto, phosphovanadic acid, germanovanadic acid, arsenovanadic acid, phosphoniobic acid, germanoniobic acid, siliconomolybdic acid, phosphomolybdic acid, titanomolybdic acid, germanomolybdic acid, arsenomolybdic acid, stannomolybdic acid, phosphotungstic acid, germanotungstic acid, stannotungstic acid, phosphomolybdovanadic acid, phosphotungstovanadic acid, germanotungstovanadic acid, phosphomolybdotungstovanadic acid, germanomolybdotungstovanadic acid, phosphomolybdotungstic acid, phosphomolybdoniobic acid; salts of these acids such as salts of these acids with metals of Group 1 or Group 2 of the periodic table such as lithium, sodium, potassium, rubidium, cesium, beryllium, magnesium, calcium, strontium and barium; organic salts of the above acids such as triphenylethyl salts; and isopoly compounds of the above salts.

The heteropoly compounds and isopoly compounds may be used singly, or two or more kinds may be used in combination.

The ionizing ionic compounds (b-3) may be used singly, or two or more kinds may be used in combination.

The olefin oligomerization catalyst according to the invention catalyzes the oligomerization of olefins with high activity. In particular, ethylene may be oligomerized into 1-hexene with high selectivity.

The olefin oligomerization catalyst containing the organoaluminum oxy-compound (b-2) such as methylaluminoxane as a cocatalyst shows very high trimerization activity with respect to ethylene. Consequently, 1-hexene is produced with high selectivity. The high activity and good selectivity in the oligomerization of ethylene into 1-hexene may be also achieved by the use of the ionizing ionic compound (b-3) such as triphenylcarbonium tetrakis(pentafluorophenyl) borate as a cocatalyst.

The olefin oligomerization catalyst contains the transition metal complex compound [A] and optionally contains at least one compound [B] selected from the organometallic compounds (b-1), the organoaluminum oxy-compounds (b-2) and the ionizing ionic compounds (b-3). Furthermore, the olefin oligomerization catalyst may contain a carrier [C] described below as required.

[Carriers [C]]

The carrier [C] optionally used in the invention is an inorganic or organic compound in the form of granular or fine particulate solid. In the invention, the carrier [C] supports the compound [A] and/or the compound [B]. Preferred inorganic compounds include porous oxides, inorganic halides, clays, clay minerals and ion-exchange layered compounds.

Examples of the porous oxides include $SiO_2$, $Al_2O_3$, MgO, ZrO, $TiO_2$, $B_2O_3$, CaO, ZnO, BaO, $ThO_2$, and complex compounds or mixtures containing these oxides, such as natural or synthetic zeolite, $SiO_2$—MgO, $SiO_2$—$Al_2O_3$, $SiO_2$—$TiO_2$, $SiO_2$—$V_2O_5$, $SiO_2$—$Cr_2O_3$ and $SiO_2$—$TiO_2$—MgO. Of these, compounds containing $SiO_2$ and/or $Al_2O_3$ as a main component are preferable.

The inorganic oxides may contain small amounts of carbonate, sulfate, nitrate and oxide components such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2O$.

The porous oxides have different properties depending on type and preparation process. The carrier used in the invention preferably has a particle diameter of 0.5 to 300 μm, preferably 20 to 200 μm, a specific surface area of 50 to 1,000 $m^2/g$, preferably 100 to 700 $m^2/g$, and a pore volume of 0.3 to 3.0 $cm^3/g$. If necessary, the carrier may be calcined at 100 to 1,000° C., and preferably 150 to 700° C. prior to use.

Examples of the inorganic halides include $MgCl_2$, $MgBr_2$, $MnCl_2$ and $MnBr_2$. The inorganic halides may be used as they are, or may be used after pulverized with, for example, a ball mill or an oscillating mill. The inorganic halides may be dissolved in a solvent such as alcohol and precipitated as fine particles with a precipitating agent.

The clays for use as the carriers in the invention are mainly composed of clay minerals. The ion-exchange layered-compounds are compounds having a crystal structure wherein planes formed by ionic bonding or the like are piled on one another in parallel with a weak bond strength, and wherein the ions contained therein are exchangeable. Most clay minerals are ion-exchange layered compounds. The clays, the clay minerals and the ion-exchange layered compounds used in the invention are not limited to natural compounds but include synthetic products.

Examples of such clays, clay minerals and ion-exchange layered compounds include clays, clay minerals and ion crystalline compounds having layered crystal structures such as hexagonal closest packing structure, antimony structure, $CdCl_2$ structure and $CdI_2$ structure.

Specific examples of the clays and the clay minerals include kaolin, bentonite, kibushi clay, gairome clay, allophane, hisingerite, pyrophyllite, mica, montmorillonite, vermiculite, chlorite, palygorskite, kaolinite, nacrite, dickite and halloysite. Specific examples of the ion-exchange layered compounds include salts of polyvalent metals and crystalline acids such as α-Zr$(HAsO_4)_2.H_2O$, α-Zr$(KPO_4)_2.3H_2O$, α-Ti$(HPO_4)_2$, α-Ti$(HAsO_4)_2.H_2O$, α-Sn$(HPO_4)_2.H_2O$, γ-Zr$(HPO_4)_2$, γ-Ti$(HPO_4)_2$ and γ-Ti $(NH_4PO_4)_2.H_2O$.

The clays, the clay minerals and the ion-exchange layered compounds preferably have a pore volume, as measured on pores having a radius of not less than 20 Å by a mercury penetration method, of not less than 0.1 cc/g, and particularly preferably 0.3 to 5 cc/g. The pore volume is measured on pores having a radius of 20 to $3\times10^4$ Å by a mercury penetration method using a mercury porosimeter. Achieving high oligomerization activity tends to be difficult if the carrier has a pore volume of less than 0.1 cc/g as measured on pores having a radius of not less than 20 Å.

It is also preferable that the clays and the clay minerals are subjected to chemical treatments. Any chemical treatments, for example, a surface treatment to remove impurities on the surface and a treatment to modify the crystal structure of clay, are employable. Examples of such chemical treatments include acid treatment, alkali treatment, salt treatment and organic substance treatment. The acid treatment removes impurities from the surface and also causes the elution of cations such as Al, Fe and Mg in the crystal structure to increase the surface area. The alkali treatment destroys the crystal structure of clay to bring about change in the structure of the clay. The salt treatment and the organic substance treatment produce, for example, ionic composites, molecular composites or organic derivatives to change the surface area or the interlayer distance.

The ion-exchange layered compound may be a layered compound in which the exchangeable ions between layers have been exchanged with other large and bulky ions utilizing ion exchange properties to enlarge the distance between the layers. The bulky ions play a pillar-like roll to support the layered structure and are generally called pillars. The introduction of other substances between layers of a layered compound is called intercalation. Examples of the guest compounds to be intercalated include cationic inorganic compounds such as $TiCl_4$ and $ZrCl_4$; metal alkoxides such as $Ti(OR)_4$, $Zr(OR)_4$, $PO(OR)_3$ and $B(OR)_3$ (R is a hydrocarbon group or the like); and metal hydroxide ions such as $[Al_{13}O_4(OH)_{24}]^{7+}$, $[Zr_4(OH)_{14}]^{2+}$ and $[Fe_3O(OCOCH_3)_6]^+$.

These compounds may be used singly, or two or more kinds may be used in combination.

The intercalation of the above compounds may be carried out in the presence of dimers obtained by hydrolysis of metal alkoxides such as $Si(OR)_4$, $Al(OR)_3$ and $Ge(OR)_4$ (R is a hydrocarbon group or the like) or in the presence of colloidal inorganic compounds such as $SiO_2$. Examples of the pillars include oxides produced by intercalation of the above metal hydroxide ions between layers followed by thermal dehydration.

The clays, the clay minerals and the ion-exchange layered compounds may be used as they are, or may be used after subjected to ball milling, sieving or the like. Moreover, they may be used after subjected to water adsorption or thermal dehydration. The clays, the clay minerals and the ion-exchange layered compounds may be used singly, or two or more kinds may be used in combination.

Of the above-mentioned materials, the clays and the clay minerals are preferable, and montmorillonite, vermiculite, hectorite, tenorite and synthetic mica are particularly preferable.

Examples of the organic compounds in the invention include granular or fine particulate solid compounds having a particle diameter of 10 to 300 μm. Such compounds include (co)dimers produced using C2-14 α-olefins such as ethylene, propylene, 1-butene and 4-methyl-1-pentene as main components, (co)dimers produced using vinylcyclohexane or styrene as a main component, and modified products of these dimers.

The olefin oligomerization catalyst contains the transition metal complex compound [A] and optionally contains at least one compound [B] selected from the organometallic compounds (b-1), the organoaluminum oxy-compounds (b-2) and the ionizing ionic compounds (b-3), and the carrier [C]. Moreover, the olefin oligomerization catalyst may contain an organic compound component [D] described below as required. [Organic compound components [D]]

In the present invention, the organic compound components [D] may be optionally used to improve oligomerization performance. Examples of the organic compounds include, but are not limited to, alcohols, phenolic compounds, carboxylic acids, phosphorus compounds and sulfonates.

The alcohols and the phenolic compounds include compounds represented by $R^{18}$—OH ($R^{18}$ is a hydrocarbon group of 1 to 50 carbon atoms or a halogenated hydrocarbon group of 1 to 50 carbon atoms). Preferred alcohols are those represented by the above formula wherein $R^{18}$ is a halogenated hydrocarbon group. Preferred phenolic compounds are those wherein the α,α'-positions in the hydroxyl group are substituted with hydrocarbon groups of 1 to 20 carbon atoms.

The carboxylic acids include those represented by $R^{19}$—COOH ($R^{19}$ is a hydrocarbon group of 1 to 50 carbon atoms or a halogenated hydrocarbon group of 1 to 50 carbon atoms, and particularly preferably a halogenated hydrocarbon group of 1 to 50 carbon atoms).

Preferred phosphorus compounds include phosphoric acids having a P—O—H bond, phosphates having a P—OR bond or a P═O bond, and phosphine oxide compounds.

The sulfonates may be represented by Formula (VI).

[Chem. 22]

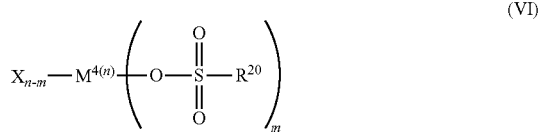

(VI)

In the above formula, $M^4$ is an atom of Group 1 to Group 14 of the periodic table; $R^{20}$ is a hydrogen atom, a hydrocarbon group of 1 to 20 carbon atoms or a halogenated hydrocarbon group of 1 to 20 carbon atoms; X is a hydrogen atom, a halogen atom, a hydrocarbon group of 1 to 20 carbon atoms or a halogenated hydrocarbon group of 1 to 20 carbon atoms; m is an integer of 1 to 7; n is a valence of M; and $1 \leq n \leq 7$.

The olefin oligomerization catalysts according to the present invention may be used in the oligomerization of olefins. Preferred olefins include vinyl compounds such as ethylene, propylene, 1-butene, 1-pentene, 1-hexene, 4-methyl-1-pentene, vinylcyclohexene, styrene, 1-octene and 1-decene; and internal olefins such as 2-butene, cyclopentene, cyclohexene and norbornene, with ethylene being particularly preferable. A plurality of the olefins may be cooligomerized.

In the processes for producing olefin oligomers according to the present invention, olefins are oligomerized in the presence of the olefin oligomerization catalysts as described hereinbelow.

[Processes for Producing Olefin Oligomers]

The olefin oligomerization processes of the invention will be described below.

In the processes for producing olefin oligomers according to the present invention, olefins are oligomerized, preferably trimerized in the presence of the aforementioned olefin oligomerization catalyst.

In a preferred embodiment, ethylene is oligomerized. In a particularly preferred embodiment, ethylene is trimerized into 1-hexene.

In the oligomerization, the transition metal complex compound [A] (hereinafter, simply referred to as the component [A]) may be added to a reactor by any methods, and the components may be handled and added by any methods in any order. Exemplary methods are given below.

(1) The component [A] alone is added to a reactor.

(2) The component [A] and at least one component [B] selected from the organometallic compound (b-1), the organoaluminum oxy-compound (b-2) and the ionizing ionic compound (b-3) (hereinafter, simply referred to as the component [B]) are added to a reactor in any order.

(3) A catalyst obtained by bringing the component [A] and the component [B] into contact with each other is added to a reactor.

(4) The component [A] and the component [B] are brought into contact with each other. The resultant catalyst component and the component [B] are added to a reactor in any order: In this case, the components [B] may be the same or different.

(5) A catalyst component in which the component [A] is supported on the carrier [C] is added to a reactor.

(6) A catalyst component in which the component [A] is supported on the carrier [C], and the component [B] are added to a reactor in any order.

(7) A catalyst in which the components [A] and [B] are supported on the carrier [C] is added to a reactor.

(8) A catalyst component in which the components [A] and [B] are supported on the carrier [C], and the component [B] are added to a reactor in any order. In this case, the components [B] may be the same or different.

(9) A catalyst component in which the component [B] is supported on the carrier [C], and the component [A] are added to a reactor in any order.

(10) A catalyst component in which the component [B] is supported on the carrier [C], and the component [A] and the component [B] are added to a reactor in any order. In this case, the components [B] may be the same or different.

(11) A catalyst component in which the component [A] is supported on the carrier [C], and a catalyst component in which the component [B] is supported on the carrier [C] are added to a reactor in any order.

(12) A catalyst component in which the component [A] is supported on the carrier [C], a catalyst component in which the component [B] is supported on the carrier [C], and the component [B] are added to a reactor in any order. In this case, the components [B] may be the same or different.

(13) The component [A] and the organic compound component [D] (hereinafter, simply referred to as the component [D]) are added to a reactor in any order.

(14) The components [A], [B] and [D] are added to a reactor in any order.

(15) The components [B] and [D] are brought into contact with each other. The resultant catalyst component and the component [A] are added to a reactor in any order.

(16) A catalyst component in which the component [D] is supported on the carrier [C], and the component [A] are added to a reactor in any order.

(17) A catalyst component in which the components [B] and [D] are supported on the carrier [C], and the component [A] are added to a reactor in any order.

(18) The components [A] and [B] are brought into contact with each other. The resultant catalyst component and the component [D] are added to a reactor in any order.

(19) The components [A] and [B] are brought into contact with each other. The resultant catalyst component, the component [B] and the component [D] are added to a reactor in any order. In this case, the components [B] may be the same or different.

(20) A catalyst component in which the components [A] and [B] are in contact with each other, and a catalyst component in which the components [B] and [D] are in contact with each other are added to a reactor in any order. In this case, the components [B] may be the same or different.

(21) A catalyst component in which the component [A] is supported on the carrier [C], and the component [B] and the component [D] are added to a reactor in any order.

(22) A catalyst component in which the component [A] is supported on the carrier [C], and the component [D] are added to a reactor in any order.

(23) A catalyst component in which the component [A] is supported on the carrier [C], and a catalyst component in which the components [B] and [D] are in contact with each other are added to a reactor in any order.

(24) A catalyst in which the components [A] and [D] are in contact with each other is added to a reactor.

(25) A catalyst obtained by bringing the components [A], [B] and [D] in any order is added to a reactor.

(26) The components [A], [B] and [D] are brought into contact with each other in any order. The resultant catalyst component and the component [B] are added to a reactor in any order. In this case, the components [B] may be the same or different.

(27) A catalyst in which the components [A] and [D] are supported on the carrier [C] is added to a reactor.

(28) A catalyst in which the components [A], [B] and [D] are supported on the carrier [C] is added to a reactor.

(29) A catalyst component in which the components [A], [B] and [D] are supported on the carrier [C], and the component [B] are added to a reactor in any order. In this case, the components [B] may be the same or different.

In the olefin oligomerization processes of the invention, olefins are oligomerized into olefin oligomers in the presence of the olefin oligomerization catalysts. The oligomerization may be carried out by liquid-phase reaction such as solution reaction or suspension reaction, or by gas-phase reaction.

The liquid-phase oligomerization may involve inert hydrocarbon solvents. Examples of the inert hydrocarbon solvents include aliphatic hydrocarbons such as propane, butane, isobutane, pentane, isopentane, hexane, heptane, octane, decane, dodecane and kerosine; alicyclic hydrocarbons such as cyclopentane, cyclohexane and methylcyclopentane; aromatic hydrocarbons such as benzene, toluene, xylene, trimethylbenzene and tetralin; halogenated hydrocarbons such as ethylene chloride, chlorobenzene and dichloromethane; and mixtures of these solvents. Of these, pentane, n-hexane and n-heptane are particularly preferred.

In the production of 1-hexene by trimerizing ethylene with the olefin oligomerization catalyst, the component [A] is generally used such that the amount thereof per liter of the reaction volume is in the range of $10^{-12}$ to $10^{-2}$ mol, and preferably $10^{-10}$ to $10^{-3}$ mol. In the invention, olefin oligomers may be obtained with high oligomerization activity even when the component [A] is used in a relatively low concentration.

When the component [B], for example the component (b-1) is used, the amount thereof is such that the molar ratio [(b-1)/M] of the component (b-1) to the transition metal atom (M) in the component [A] is generally in the range, of 0.01 to 100000, and preferably 0.05 to 50000.

The component (b-2) may be used such that the molar ratio [(b-2)/M] of the aluminum atom in the component (b-2) to the transition metal atom (M) in the component [A] is generally in the range of 10 to 500000, and preferably 20 to 100000.

The component (b-3) may be used such that the molar ratio [(b-3)/M] of the component (b-3) to the transition metal atom (M) in the component [A] is generally in the range of 1 to 10, and preferably 1 to 5.

The component [C] may be used such that the ratio (g/mol) of the mass (g) of the component [C] to the mol of the transition metal atom (M) in the component [A] is generally in the range of 100 to 10000, and preferably 1000 to 5000.

The component [D] may be used in amounts such that: when the component [B] is the component (b-1), the molar ratio [[D]/(b-1)] is generally in the range of 0.01 to 10, and preferably 0.1 to 5; when the component [B] is the component (b-2), the molar ratio [[D]/(b-2)] of the component [D] to the aluminum atom in the component (b-2) is generally in the range of 0.001 to 2, and preferably 0.005 to 1; and when the component [B] is the component (b-3), the molar ratio [[D]/(b-3)] is generally in the range of 0.01 to 10, and preferably 0.1 to 5.

The reaction temperature in the olefin oligomerization with the olefin oligomerization catalyst is usually in the range of −50 to 200° C., and preferably 0 to 170° C. The reaction pressure is generally from atmospheric pressure to 10 MPa, and preferably atmospheric pressure to 5 MPa. The oligomerization reaction may be carried out batchwise, semi-continuously or continuously.

An antistatic agent may be used in the olefin oligomerization with the olefin oligomerization catalyst. Preferred examples of the antistatic agents include polypropylene glycol, polypropylene glycol distearate, ethylenediamine-PEG-PPG block copolymer, stearyldiethanolamine, lauryldiethanolamine, alkyl diethanolamides and polyoxyalkylenes (such as polyethylene glycol-polypropylene glycol-polyethylene glycol block copolymer (PEG-PPG-PEG)), with the polyoxyalkylenes (PEG-PPG-PEG) being particularly preferable. The antistatic agent may be used such that the ratio (g/mol) of the mass (g) of the antistatic agent to the mol of the transition metal atom (M) in the component [A] is generally in the range of 100 to 10000, and preferably 100 to 1000.

Hydrogen may be used in the olefin oligomerization with the olefin oligomerization catalyst. The pressure of hydrogen in the reaction is 0.01 to 5 MPa, and preferably 0.01 to 1 MPa.

EXAMPLES

The present invention will be described based on examples below without limiting the scope of the invention.

The yield of the reaction product and the selectivity for 1-hexene were determined by gas chromatography (Shimadzu GC-14A, J&W Scientific DB-5 column).
[Catalytic Activity]

The mass of the reaction product obtained per unit time was divided by the amount (mmol) of the transition metal atom in the transition metal catalyst component used in the oligomerization.
[Selectivity for 1-hexene]

The selectivity for 1-hexene was determined by the following formula:

$$S(\%)=Wp/Wr \times 100$$

S (%): Selectivity for 1-hexene (weight fraction)
Wr (weight): Total weight of reaction products having 4 or more carbon atoms
Wp (weight): Weight of 1-hexene produced by the reaction
Synthetic Examples for the transition metal complex compounds [A], and Examples and Comparative Examples of ethylene oligomerization will be described below.

Example 1

(Synthesis of Compound 1)

[Chem. 23]

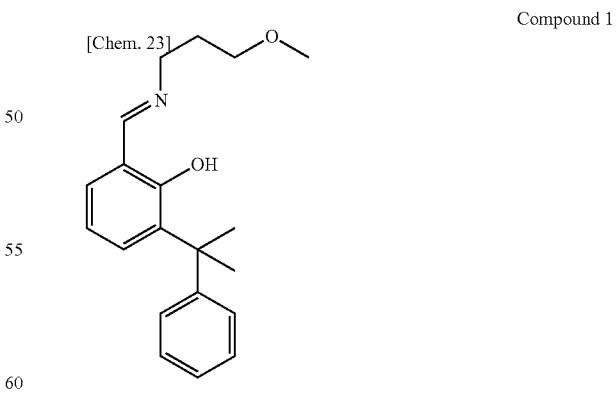

Compound 1

In a thoroughly dried 100 ml eggplant flask (equipped with a three-way cock and a magnetic stirrer), 0.62 ml (6.0 mmol) of 3-methoxypropan-1-amine and 1.20 g (5.0 mmol) of 2-hydroxy-3-(2-phenylpropan-2-yl)benzaldehyde were dissolved in 20 ml of ethanol. Reaction was carried out for 6 hours at room temperature. The reaction liquid was distilled under reduced pressure to remove the solvent, resulting in 1.63 g of Compound 1 (100% yield, orange colored oil).

The product was analyzed, and the results were as follows.

$^1$H NMR (δ, CDCl$_3$): 13.63 (s, 1H, OH), 8.29 (s, 1H, N=CH), 7.49 (d, J=1.6 Hz, 1H, Ar—H), 7.46-7.12 (m, 6H, Ar—H), 6.88 (t, J=7.9, 7.6 Hz, 1H, Ar—H), 3.56 (t, J=5.9 Hz, 2H, CH$_2$), 3.38 (t, J=6.2, 5.9 Hz, 2H, CH$_2$), 3.29 (s, 3H, CH$_3$), 1.92-1.82 (m, 2H, CH$_2$), 1.74 (s, 6H, C(CH$_3$)$_2$).

(Synthesis of Compound 2)

[Chem. 24]

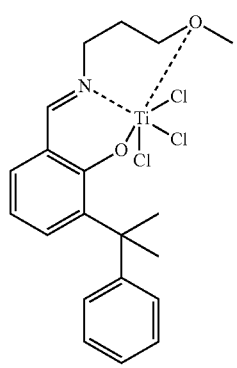

Compound 2

In a thoroughly dried 50 ml two-necked eggplant flask (equipped with a three-way cock and a magnetic stirrer), 311 mg (1.0 mmol) of Compound 1 was dissolved in 10 ml of diethyl ether. The mixture liquid was cooled to −78° C., and 0.63 ml (1.0 mmol) of 1.6 mol/L hexane solution of n-butyllithium was added dropwise to the liquid. Reaction was carried out for 1 hour while gradually increasing the temperature to room temperature. To the reaction liquid, 0.5 ml (4.0 mmol) of trimethylsilyl chloride was added, and reaction was carried out for 15 hours at room temperature. The reaction liquid was filtered through a glass filter, and the solvent was evaporated, resulting in a yellow oil. The oil was dissolved in 5 ml of dichloromethane. Separately, 1.0 ml (1.0 mmol) of 1.0 mol/L dichloromethane solution of titanium tetrachloride and 10 ml of dichloromethane were placed in a thoroughly dried 50 ml two-necked eggplant flask (equipped with a three-way cock and a magnetic stirrer). The solution of the yellow oil was added dropwise to the mixture in the eggplant flask at −78° C. Reaction was carried out for 4 hours while gradually increasing the temperature to room temperature. The reaction liquid was then concentrated to approximately 5 ml, and 20 ml of pentene was added thereto to precipitate a solid. The solid was filtered out and was washed with pentene. Consequently, 292 mg of Compound 2 was obtained (63% yield, orange solid).

The product was analyzed, and the results were as follows.

$^1$H NMR spectrum of the compound is shown in FIG. 1.

$^1$H NMR (δ, CDCl$_3$): 8.06 (s, 1H, N=CH), 7.58 (d, J=7.9 Hz, 1H, Ar—H), 7.32-7.06 (m, 7H, Ar—H), 4.35 (t, J=5.6, 5.3 Hz, 2H, CH$_2$), 4.13 (s, 3H, CH$_3$), 3.91 (bs, 2H, CH$_2$), 2.20 (bs, 2H, CH$_2$), 1.79 (s, 6H, C(CH$_3$)$_2$).

FD-MS: m/z=463 (M$^+$, C$_{20}$H$_{24}$Cl$_3$NO$_2$Ti)

Example 2

(Synthesis of Compound 3)

[Chem. 25]

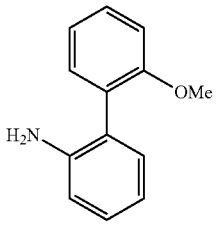

Compound 3

In a thoroughly dried 200 ml two-necked eggplant flask (equipped with a condenser, a three-way cock and a magnetic stirrer), 3.44 g (20 mmol) of 2-methoxyphenylboronic acid, 3.19 g (21 mmol) of 2-bromobenzenamine, 0.355 g (2.0 mmol) of palladium chloride, 1.05 g (4.0 mmol) of triphenylphosphine and 30 mmol of potassium carbonate were suspended in 50 ml of toluene. Reaction was carried out for 9.5 hours at 100° C. The reaction liquid was combined with 50 ml of water and extracted with toluene. The organic phase was dried over MgSO$_4$ and was concentrated to give 6.3 g of a crude product. The crude product was purified by silica gel column chromatography (eluting solution: hexane/ethyl acetate=3/1) to afford 1.76 g of Compound 3 (44% yield, yellow solid).

The product was analyzed, and the results were as follows.

$^1$H NMR (δ, CDCl$_3$): 7.38-6.98 (m, 6H, Ar—H), 6.85-6.75 (m, 2H, Ar—H), 3.80 (s, 3H, CH$_3$), 3.67 (br, 2H, NH$_2$).

(Synthesis of Compound 4)

[Chem. 26]

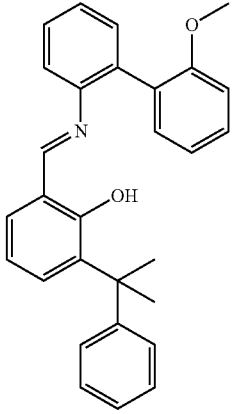

Compound 4

In a thoroughly dried 100 ml eggplant flask (equipped with a three-way cock and a magnetic stirrer), 598 mg (3.0 mmol) of Compound 3 and 721 mg (3.0 mmol) of 2-hydroxy-3-(2-phenylpropan-2-yl)benzaldehyde were dissolved in 15 ml of ethanol. Reaction was carried out for 18 hours at room temperature. The reaction liquid was distilled under reduced pressure to remove the solvent. The distillate was recrystallized in methanol, and the crystal was further recrystallized in hexane. Consequently, 240 mg of Compound 4 was obtained (19% yield, yellow solid).

The product was analyzed, and the results were as follows.

$^1$H NMR (δ, CDCl$_3$): 13.21 (s, 1H, OH), 8.44 (s, 1H, N=CH), 7.50-6.58 (m, 16H, Ar—H), 3.32 (s, 3H, CH$_3$), 1.51 (s, 6H, C(CH$_3$)$_2$)

(Synthesis of Compound 5)

[Chem. 27]

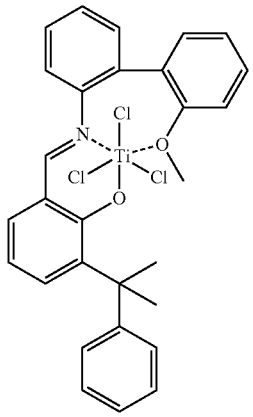

Compound 5

In a thoroughly dried 50 ml two-necked eggplant flask (equipped with a three-way cock and a magnetic stirrer), 240 mg (0.57 mmol) of Compound 4 was dissolved in 5 ml of diethyl ether. The mixture liquid was cooled to −78° C., and 0.36 ml (0.57 mmol) of 1.6 mol/L hexane solution of n-butyllithium was added dropwise to the liquid. Reaction was carried out for 1 hour while gradually increasing the temperature to room temperature. To the reaction liquid, 0.5 ml (4.0 mmol) of trimethylsilyl chloride was added, and reaction was carried out for 2 hours at room temperature. The reaction liquid was filtered through a glass filter, and the solvent was evaporated, resulting in a yellow oil. The oil was dissolved in 5 ml of dichloromethane. Separately, 0.57 ml (0.57 mmol) of 1.0 mol/L dichloromethane solution of titanium tetrachloride and 5 ml of dichloromethane were placed in a thoroughly dried 50 ml two-necked eggplant flask (equipped with a three-way cock and a magnetic stirrer). The solution of the yellow oil was added dropwise to the mixture in the eggplant flask at −78° C. Reaction was carried out for 8 hours while gradually increasing the temperature to room temperature. The reaction liquid was then concentrated to approximately 2 ml, and 20 ml of pentane was added thereto to precipitate a solid. The solid was filtered out and was washed with pentane. Consequently, 58 mg of Compound 5 was obtained (18% yield, orange solid).

The product was analyzed, and the results were as follows.

$^1$H NMR spectrum of the compound is shown in FIG. 2.

$^1$H NMR (δ, CDCl$_3$): 7.95 (s, 1H, N=CH), 7.67 (d, J=7.6 Hz, 1H, Ar—H), 7.42-6.98 (m, 15H, Ar—H), 4.10 (s, 3H, CH$_3$), 1.87 (s, 3H, C(CH$_3$)$_2$), 1.70 (s, 3H, C(CH$_3$)$_2$).

FD-MS: m/z=523 (M$^+$-CH$_3$Cl, C$_{28}$H$_{23}$Cl$_2$NO$_2$Ti)

Example 3

(Synthesis of Compound 6)

[Chem. 28]

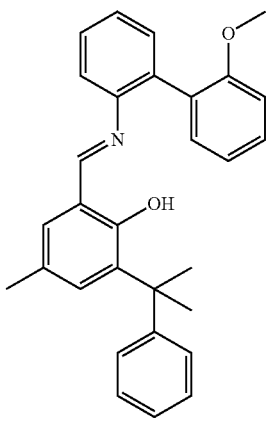

Compound 6

In a thoroughly dried 100 ml eggplant flask (equipped with a three-way cock and a magnetic stirrer), 877 mg (4.4 mmol) of Compound 3 and 1.02 g (4.0 mmol) of 2-hydroxy-5-methyl-3-(2-phenylpropan-2-yl)benzaldehyde were dissolved in 20 ml of ethanol. Two droplets of acetic acid were added, and reaction was carried out for 18 hours at room temperature. The reaction liquid was distilled under reduced pressure to remove the solvent. The distillate was recrystallized in methanol, and the crystal was further recrystallized in hexane. Consequently, 1.29 g of Compound 6 was obtained (74% yield, yellow solid).

The product was analyzed, and the results were as follows.

$^1$H NMR (δ, CDCl$_3$): 12.92 (s, 1H, OH), 8.38 (s, 1H, N=CH), 7.38-7.07 (m, 12H, Ar—H), 6.98 (s, 1H, Ar—H), 6.89 (t, J=7.6, 7.2 Hz, 1H, Ar—H), 6.58 (d, J=8.2 Hz, 1H, Ar—H), 3.31 (s, 3H, OCH$_3$), 2.32 (s, 3H, CH$_3$), 1.65 (s, 6H, C(CH$_3$)$_2$).

(Synthesis of Compound 7)

[Chem. 29]

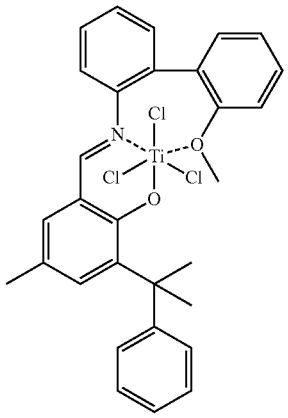

Compound 7

In a thoroughly dried 50 ml two-necked eggplant flask (equipped with a three-way cock and a magnetic stirrer), 436 mg (1.0 mmol) of Compound 6 was dissolved in 10 ml of diethyl ether. The mixture liquid was cooled to −78° C., and 0.63 ml (1.0 mmol) of 1.6 mol/L hexane solution of n-butyllithium was added dropwise to the liquid. Reaction was carried out for 1.5 hours while gradually increasing the temperature to room temperature. To the reaction liquid, 0.5 ml (4.0 mmol) of trimethylsilyl chloride was added, and reaction was carried out for 12 hours at room temperature. The reaction liquid was filtered through a glass filter, and the solvent was evaporated, resulting in a yellow oil. The oil was dissolved in 5 ml of dichloromethane. Separately, 1.0 ml (1.0 mmol) of 1.0 mol/L dichloromethane solution of titanium tetrachloride and 5 ml of dichloromethane were placed in a thoroughly dried 50 ml two-necked eggplant flask (equipped with a three-way cock and a magnetic stirrer). The solution of the yellow oil was added dropwise to the mixture in the eggplant flask at −78° C. Reaction was carried out for 8 hours while gradually increasing the temperature to room temperature, and 20 ml of hexane was added to precipitate a solid. The solid was filtered out and was washed with hexane. Consequently, 245 mg of a mixture of isomeric Compounds 7 was obtained (42% yield, orange solid).

The product was analyzed, and the results were as follows.
$^1$H NMR spectrum of the compound is shown in FIG. 3
$^1$H NMR (δ, CDCl$_3$): (of the predominant isomer) 7.90 (s, 1H, N═CH), 7.47-6.99 (m, 15H, Ar—H), 4.09 (s, 3H, OCH$_3$), 2.31 (s, 3H, CH$_3$), 1.85 (s, 3H, C(CH$_3$)$_2$) 1.67 (s, 3H, C(CH$_3$)$_2$).
FD-MS: m/z=537 (M$^+$-CH$_3$Cl, C$_{29}$H$_{25}$Cl$_3$NO$_2$Ti)

Example 4

(Synthesis of Compound 8)

[Chem. 30]

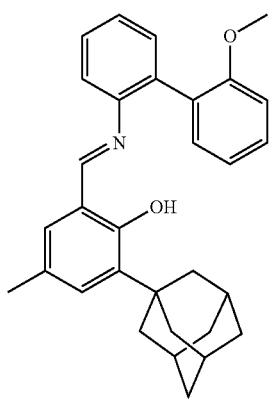

Compound 8

In a thoroughly dried 100 ml eggplant flask (equipped with a three-way cock and a magnetic stirrer), 2.23 g (11.3 mmol) of Compound 3 and 3.06 g (11.3 mmol) of 2-hydroxy-5-methyl-3-(1-adamantyl)benzaldehyde were dissolved in 50 ml of toluene. Further, 10 mg of paratoluenesulfonic acid was added, and reaction was carried out for 17 hours at 110° C. The reaction liquid was distilled under reduced pressure to remove the solvent. The distillate was recrystallized in ethanol to afford 2.87 g of Compound 8 (56% yield, yellow solid).

The product was analyzed, and the results were as follows.
$^1$H NMR (δ, CDCl$_3$): 13.02 (s, 1H, OH), 8.48 (s, 1H, N═CH), 7.45-6.85 (m, 8H, Ar—H), 3.75 (s, 3H, OCH$_3$), 2.25 (s, 3H, CH$_3$), 2.11 (s, 6H, CH$_2$), 2.10 (s, 3H, CH), 1.78 (s, 6H, CH$_2$).

(Synthesis of Compound 9)

[Chem. 31]

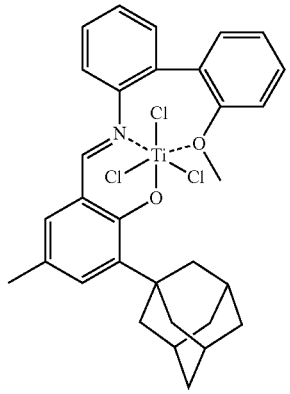

Compound 9

A thoroughly dried and nitrogen-purged 100 ml two-necked eggplant flask (equipped with a three-way cock and a magnetic stirrer) was charged with 50 ml of toluene and 6.2 ml of 1.0 M toluene solution of titanium tetrachloride. The resultant solution was cooled to −78° C., and 25 ml of a toluene solution containing 2.80 g (6.20 mmol) of Compound 8 was added dropwise to the solution over a period of 20 minutes. Reaction was carried out for 12 hours while gradually increasing the temperature to room temperature. The solid that precipitated after the reaction was filtered out, then washed with 5 ml of diethyl ether and dried under reduced pressure to give 3.08 g of Compound 9 (82% yield, red-brown solid).

The product was analyzed, and the results were as follows.
$^1$H-NMR (δ, CDCl$_3$): 8.11 (s, 3H), 7.58-7.04 (m, 10H), 4.44 (s, 3H), 2.34 (s, 3H), 2.22 (bs, 6H), 2.18 (bs, 3H), 1.81 (d, 3H, 12 Hz), 1.93 (d, 3H, 12 Hz).
FD-MS: m/z=604 (M$^+$, C$_{31}$H$_{32}$Cl$_3$NO$_2$Ti)

Example 5

(Synthesis of Compound 10)

[Chem. 32]

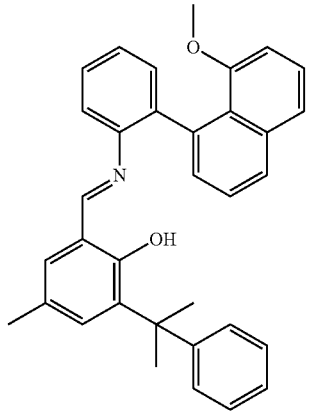

Compound 10

A thoroughly dried 50 ml eggplant flask (equipped with a three-way cock and a magnetic stirrer) was charged with 0.623 g (2.5 mmol) of 2-(8-methoxy-naphthalen-1-yl)phenylamine, 0.736 g (2.75 mmol) of 2-hydroxy-5-methyl-3-(1-methyl-1-phenyl-ethyl)benzaldehyde, 12.5 ml of ethanol and one droplet of acetic acid. Reaction was carried out for 4 hours at 60° C. Part of the solvent was evaporated under reduced pressure. The supernatant liquid was removed, and the precipitate was washed with methanol to afford 0.50 g (1.03 mmol) of Compound 10 (41% yield).

The product was analyzed, and the results were as follows.
$^1$H-NMR (δ, CDCl$_3$): 1.47 ppm (s, 3H), 1.49 ppm (s, 3H), 2.24 ppm (s, 3H), 3.29 ppm (s, 3H), 6.54-7.72 ppm (m, 17H), 8.30 ppm (s, 1H), 12.17 ppm (s, 1H).

(Synthesis of Compound 11)

[Chem. 33]

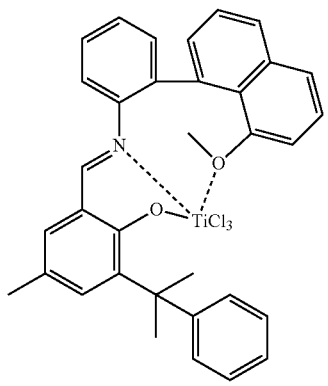

Compound 11

A 50 ml eggplant flask A (equipped with a three-way cock and a magnetic stirrer) was charged with 0.33 g (1.00 mmol) of TiCl$_4$(thf)$_2$ in a glove box. The eggplant flask A was removed from the glove box, and 4 ml of dehydrated THF was added thereto. The eggplant flask A was cooled to −78° C. in a dry ice/methanol bath. A separate 30 ml eggplant flask B (equipped with a three-way cock and a magnetic stirrer) was charged with 0.50 g (1.00 mmol) of Compound 10 and was purged with nitrogen. Thereafter, 2 ml of dehydrated THF was added to the eggplant flask B, and Compound 10 was dissolved. The THF solution of Compound 10 was added dropwise to the eggplant flask A using a cannula at −78° C. After the completion of the dropwise addition, the dry ice/methanol bath was removed, and the reaction liquid was slowly brought to room temperature. Reaction was carried out for 12 hours at room temperature, and part of the solvent was evaporated under reduced pressure. The reaction liquid was combined with 20 ml of dehydrated pentane and was filtered under a nitrogen atmosphere. The solid obtained was washed with dehydrated hexane and was dried under reduced pressure to afford 0.628 g of Compound 11.

The product was analyzed, and the results were as follows.
FD-MS: m/z=637 (M$^+$, C$_{34}$H$_{30}$NO$_2$Cl$_3$Ti)

Example 6

(Synthesis of Compound 12)

[Chem. 34]

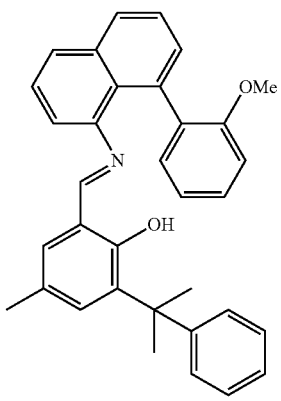

Compound 12

A thoroughly dried 50 ml eggplant flask (equipped with a three-way cock and a magnetic stirrer) was charged with 0.623 g (2.5 mmol) of 8-(2-methoxy-phenyl)-naphthalen-1-ylamine, 0.636 g (2.5 mmol) of 2-hydroxy-5-methyl-3-(1-methyl-1-phenyl-ethyl)benzaldehyde, 8 ml of ethanol and one droplet of acetic acid. Reaction was carried out for 5 hours at 60° C. and for 12 hours at room temperature. The resultant yellow precipitate was filtered out, then washed with ethanol and dried under reduced pressure to afford 1.10 g (2.33 mmol) of Compound 12 (93% yield). The product was analyzed, and the results were as follows.
$^1$H-NMR (δ, CDCl$_3$): 1.65 ppm (s, 3H), 1.74 ppm (s, 3H), 2.33 ppm (s, 3H), 3.40 ppm (s, 3H), 6.20-7.85 ppm (m, 17H), 8.03 ppm (s, 1H), 11.49 ppm (s, 1H).

(Synthesis of Compound 13)

[Chem. 35]

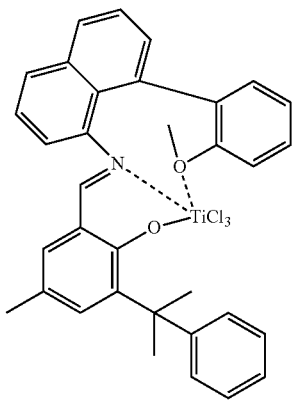

Compound 13

A 50 ml eggplant flask A (equipped with a three-way cock and a magnetic stirrer) was charged with 0.584 g (1.75 mmol) of TiCl$_4$(thf)$_2$ in a glove box. The eggplant flask A was removed from the glove box, and 5 ml of dehydrated THF was added thereto. The eggplant flask A was cooled to −78° C. in a dry ice/methanol bath. A separate 30 ml eggplant flask B (equipped with a three-way cock and a magnetic stirrer) was charged with 0.822 g (1.75 mmol) of Compound 12 and was purged with nitrogen. Thereafter, 2 ml of dehydrated THF was added to the eggplant flask B, and Compound 12 was dissolved. The THF solution of Compound 12 was added dropwise to the eggplant flask A using a cannula at −78° C. After the completion of the dropwise addition, the dry ice/methanol bath was removed, and the reaction liquid was slowly brought to room temperature. Reaction was carried out for 12 hours at room temperature, and part of the solvent was evaporated under reduced pressure. The reaction liquid was combined with 10 ml of dehydrated pentane and was filtered under a nitrogen atmosphere. The solid obtained was washed with dehydrated hexane and was dried under reduced pressure to afford 1.40 mmol of Compound 13 (80% yield).

The product was analyzed, and the results were as follows.

$^1$H NMR (δ, CDCl$_3$): 1.74 ppm (s, 3H), 2.00 ppm (s, 3H), 2.27 ppm (s, 3H), 3.87 ppm (s, 3H), 5.28 ppm (d, 1H), 6.50-7.91 ppm (m, 17H).

FD-MS: m/z=637 (M$^+$, C$_{34}$H$_{30}$NO$_2$Cl$_3$Ti)

Examples 7 to 31

Compounds 14 to 38 were synthesized in the same manner as in Examples 1 to 6. The results of analysis are shown below.

[Chem. 36]

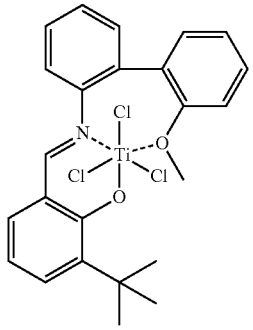

Compound 14

$^1$H NMR (δ, CDCl$_3$): 8.16 (s, 1H, N=CH), 7.64 (dd, J=7.91, 1.65 Hz, 1H, Ar—H), 7.52-7.14 (m, 9H, Ar—H), 7.07 (t, J=7.91, 7.91 Hz, 1H, Ar—H), 4.39 (s, 3H, OCH$_3$), 1.54 (s, 9H, C(CH$_3$)$_3$)

FD-MS: m/z=513 (M$^+$), 461 (M$^+$-CH$_3$Cl) C$_{24}$H$_{24}$Cl$_3$NO$_2$Ti

[Chem. 37]

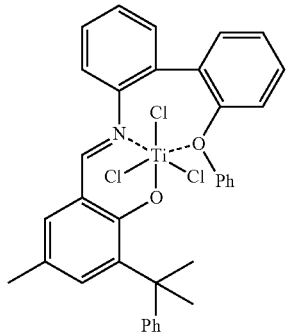

Compound 15

FD-MS: m/z=651 (M$^+$, C$_{35}$H$_{30}$Cl$_3$NO$_2$Ti)

[Chem. 38]

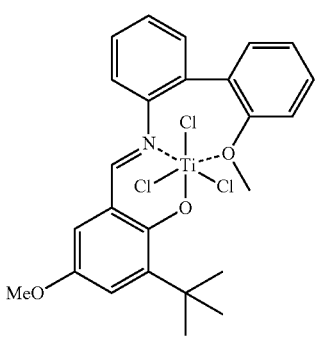

Compound 16

$^1$H NMR (δ, CDCl$_3$): 8.19 (1H), 7.59-7.19 (9H), 6.81 (1H, 2 Hz), 4.44 (3H), 3.81 (3H), 1.56 (9H).

[Chem. 39]

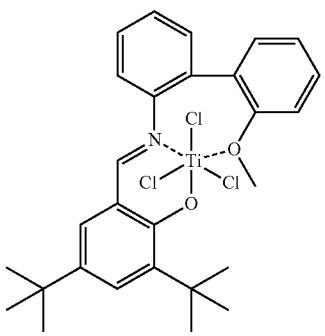

Compound 17

$^1$H NMR (δ, CDCl$_3$): 8.18 (s, 1H, N=CH), 7.80-7.15 (m, 10H, Ar—H), 4.41 (s, 3H, OCH$_3$), 1.53 (s, 9H, C(CH$_3$)$_3$), 1.28 (s, 9H, C(CH$_3$)$_3$)

[Chem. 40]

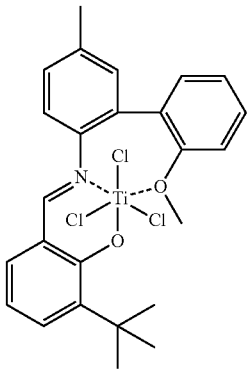

Compound 18

$^1$H NMR (δ, CDCl$_3$): 1.48 ppm (s, 9H), 2.40 ppm (s, 3H), 4.36 ppm (s, 3H), 6.98-7.60 ppm (m, 10H), 8.09 ppm (s, 1H).

FD-MS: m/z=525 (M$^+$, C$_{25}$H$_{26}$NO$_2$Cl$_3$Ti)

[Chem. 41]

Compound 19

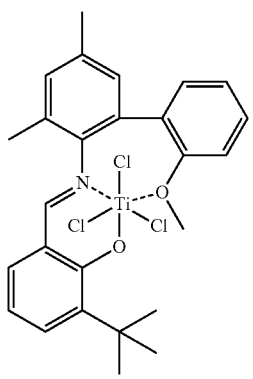

¹H NMR (δ, CDCl₃): 1.54 ppm (br, 9H), 2.43 ppm (br, 6H), 4.28 ppm (br, 3H), 6.96-7.61 ppm (m, 9H), 7.96 ppm (br, 1H).
FD-MS: m/z=539 (M⁺, $C_{26}H_{28}NO_2Cl_3Ti$).

[Chem. 42]

Compound 20

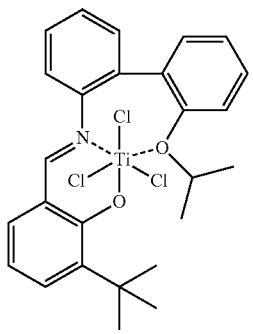

¹H NMR (δ, CDCl₃): 0.76 ppm (br, 3H), 1.46 ppm (br, 12H), 6.06 ppm (br, 1H), 6.95-7.66 ppm (m, 11H), 8.05 ppm (br, 1H).
FD-MS: m/z=461

[Chem. 43]

Compound 21

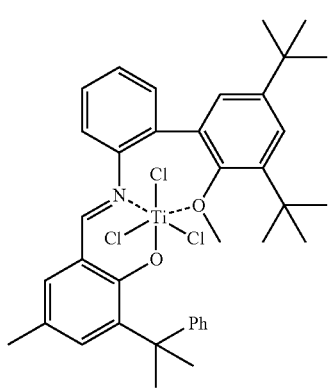

¹H NMR (δ, CDCl₃): 8.37 (bs, 1H, N=CH), 7.53-6.91 (m, 13H, Ar—H), 3.65 (bs, 3H, OCH₃), 2.36 (s, 3H, Ar—CH₃), 1.78 (s, 6H, C(CH₃)₂), 1.26 (s, 9H, C(CH₃)₃), 1.25 (s, 9H, a(CH₃)₃).
FD-MS: m/z=699 (M⁺, $C_{38}H_{44}Cl_3NO_2Ti$)

[Chem. 44]

Compound 22

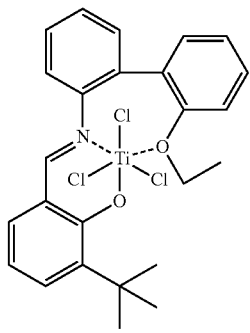

¹H NMR spectrum recorded with CDCl₃ solvent at room temperature is shown in FIG. 4.
FD-MS: m/z=525 (M⁺, $C_{25}H_{26}NO_2Cl_3Ti$)

[Chem. 45]

Compound 23

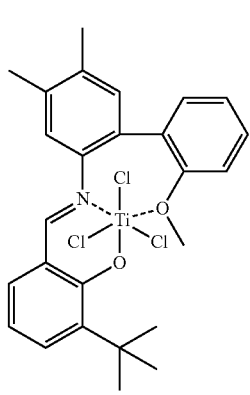

¹H-NMR (δ, CDCl₃): 1.49 ppm (s, 9H), 2.29 ppm (s, 3H), 2.30 ppm (s, 3H), 4.39 ppm (s, 3H), 6.87-7.60 ppm (m, 9H), 8.10 ppm (s, 1H).
FD-MS: m/z=539 (M⁺, $C_{26}H_{28}NO_2Cl_3Ti$)

[Chem. 46]

Compound 24

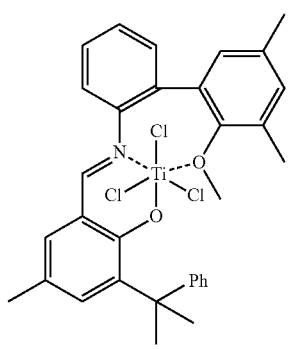

¹H NMR (δ, CDCl₃): 8.04 (s, 1H, N=CH), 7.43-6.86 (m, 13H, Ar—H), 4.16 (s, 3H, OCH₃), 2.53 (s, 3H, Ar—CH₃), 2.33 (s, 3H, Ar—CH₃), 2.29 (s, 3H, Ar—CH₃), 1.91 (s, 3H, C(CH₃)₂), 1.74 (s, 3H, C(CH₃)₂).
FD-MS: m/z=615 (M⁺, $C_{32}H_{32}Cl_3NO_2Ti$)

[Chem. 47]

Compound 25

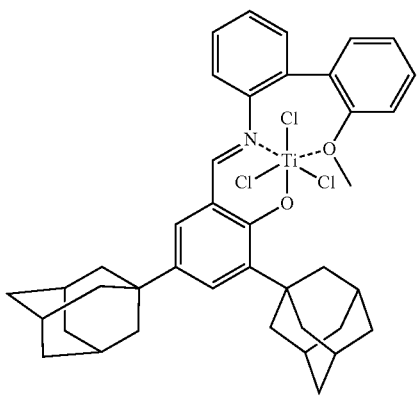

¹H NMR (δ, CDCl₃): 8.20 (s, 1H), 7.65-7.04 (m, 10H), 4.43 (s, 3H), 2.30-2.00 (m, 18H), 2.00-1.53 (m, 12H).

[Chem. 48]

Compound 26

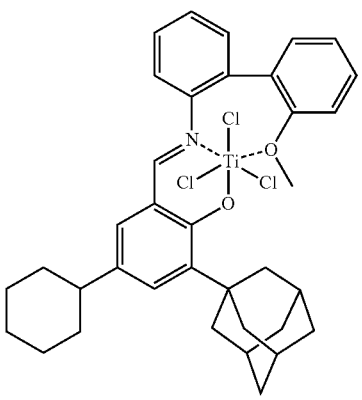

¹H NMR (δ, CDCl₃): 8.17 (s, 1H), 7.57-7.09 (s, 10H), 4.43 (s, 3H), 2.53-2.40 (m, 1H), 2.21-2.15 (m, 9H), 1.97-1.65 (m, 10H), 1.48-1.21 (m, 5H).

[Chem. 49]

Compound 27

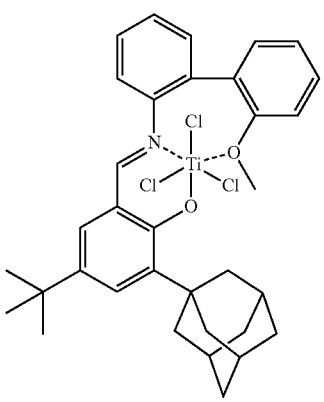

¹H NMR (δ, CDCl₃): 8.18 (s, 1H, N=CH), 7.62 (d, J=2.3 Hz, 1H, Ar—H), 7.49-7.26 (m, 8H, Ar—H), 7.15-7.11 (m, 1H, Ar—H), 4.42 (s, 3H, OCH₃), 2.22-2.16 (m, 9H, Ad-H), 1.95-1.91 (m, 3H, Ad-H), 1.81-1.77 (m, 3H, Ad-H), 1.28 (s, 9H, C(CH₃)₃).

[Chem. 50]

Compound 28

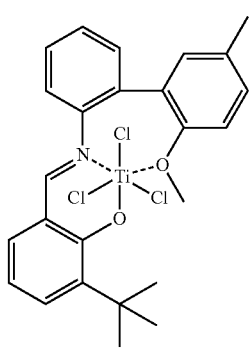

¹H-NMR (δ, CDCl₃): 1.46 ppm (s, 9H), 2.27 ppm (s, 3H), 4.29 ppm (s, 3H), 6.97-7.59 ppm (m, 10H), 8.08 ppm (s, 1H).
FD-MS: m/z=525 (M⁺, C₂₅H₂₆NO₂Cl₃Ti)

[Chem. 51]

Compound 29

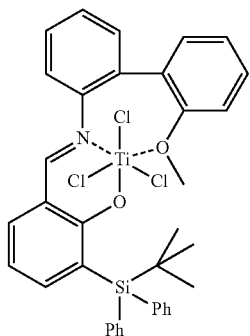

¹H NMR (δ, CDCl₃): 8.16 (s, 1H, N=CH), 7.72-7.03 (m, 21H, Ar—H), 4.31 (s, 3H, CH₃), 1.32 (s, 9H, C(CH₃)₃).
FD-MS: m/z=585 (M⁺-C₇H₈Cl, C₂₉H₂₆Cl₂NO₂SiTi)

[Chem. 52]

Compound 30

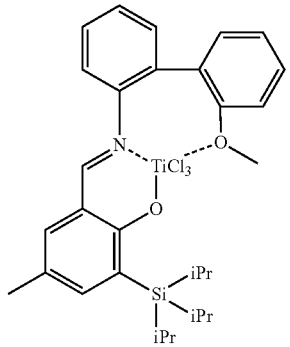

¹H NMR spectrum recorded with CDCl₃ solvent at room temperature is shown in FIG. 5.

[Chem. 53]

Compound 31

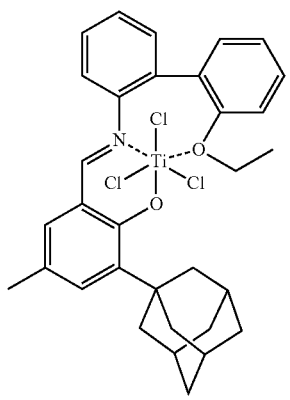

¹H NMR spectrum recorded with CDCl₃ solvent at room temperature is shown in FIG. 6.

[Chem. 54]

Compound 32

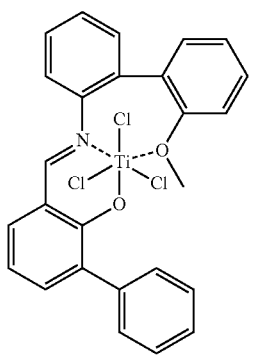

¹H NMR (δ, CDCl₃): 4.34 ppm (br, 3H), 6.94-7.70 ppm (m, 16H), 8.17 ppm (br, 1H).
FD-MS: m/z=481

[Chem. 55]

Compound 33

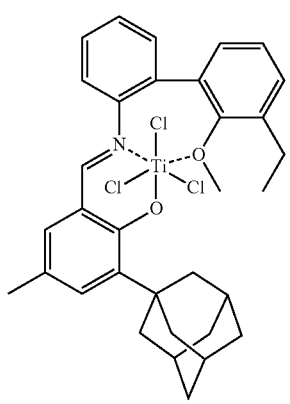

¹H NMR spectrum recorded with CDCl₃ solvent at room temperature is shown in FIG. 7.

[Chem. 56]

Compound 34

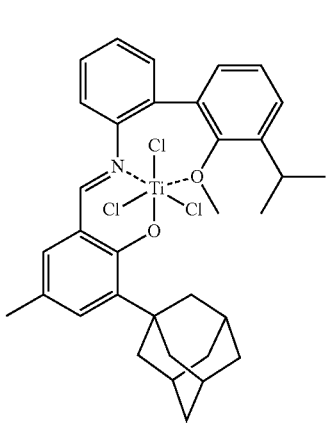

¹H NMR spectrum recorded with CDCl₃ solvent at room temperature is shown in FIG. 8.

[Chem. 57]

Compound 35

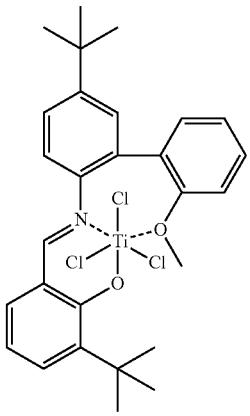

¹H NMR (δ, CDCl₃): 1.31 ppm (s, 9H), 1.46 ppm (s, 9H), 4.34 ppm (br, 3H), 6.97-7.58 ppm (m, 10H), 8.09 ppm (br, 1H).
FD-MS: m/z=567 (M⁺, $C_{28}H_{32}NO_2Cl_3Ti$)

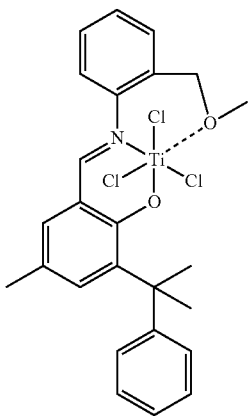

Compound 36

$^1$H NMR spectrum recorded with CDCl$_3$ solvent at room temperature is shown in FIG. 9.

Example 32

(Synthesis of Compound 39)

[Chem. 61]

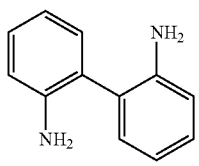

Compound 39

In a thoroughly dried 100 ml three-necked eggplant flask (equipped with a three-way cock and a magnetic stirrer), 12.2 g (50 mmol) of 2,2'-dinitrobiphenyl and 0.61 g of 5 wt % Pd/C were suspended in 75 ml of ethanol. Reaction was carried out for 44.5 hours at room temperature under a hydrogen atmosphere. The reaction liquid was filtered with Celite, and the filtrate was distilled under reduced pressure to remove the solvent, giving a crude product. The crude product was purified by silica gel column chromatography (eluting solution: hexane/ethyl acetate=6/1) to afford 6.95 g of Compound 39 (75% yield, white solid).

The product was analyzed, and the results were as follows.

$^1$H NMR (CDCl$_3$): 7.43-7.03 (m, 4H, Ar—H), 6.82-6.71 (m, 4H, Ar—H), 3.51 (br, 4H, NH$_2$).

(Synthesis of Compound 40)

[Chem. 62]

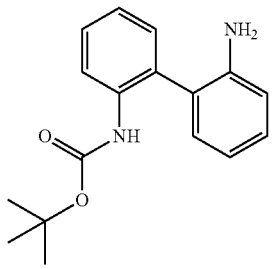

Compound 40

A 200 ml eggplant flask (equipped with a three-way cock and a magnetic stirrer) was charged with 2.22 g of sodium carbonate, 30 ml of water, 40 ml of dioxane and 3.69 g (20 mmol) of Compound 39. The temperature was lowered to 0° C. in an ice bath, and 4.37 g (20 mmol) of di-tert-butyl dicarbonate was added dropwise. Reaction was carried out for 6 hours while increasing the temperature to room temperature. Additional 2.18 g (10 mmol) of di-tert-butyl dicarbonate was added dropwise to the reaction liquid, and reaction was performed for 24 hours at room temperature. The reaction liquid was combined with 100 ml of purified water and was extracted once with 100 ml of toluene and then twice with 50 ml of toluene. The organic phase was dried over MgSO$_4$ and was distilled under reduced pressure to remove the solvent, giving a crude product. The crude product was purified by silica gel column chromatography (eluting solution: hexane/ethyl acetate=6/1) to afford 3.07 g of Compound 40 (50% yield, white solid).

The product was analyzed, and the results were as follows.

$^1$H NMR (CDCl$_3$): 7.99 (d, J=6.8 Hz, 1H), 7.27-6.81 (m, 7H, Ar—H), 6.54 (s, 1H, NH), 3.58 (br, 2H, NH$_2$), 1.37 (s, 9H, C(CH$_3$)$_3$).

(Synthesis of Compound 41)

[Chem. 63]

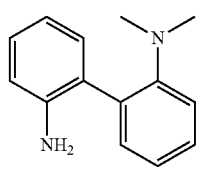

Compound 41

A 200 ml eggplant flask (equipped with a three-way cock and a magnetic stirrer) was charged with 2.22 g of sodium carbonate, 30 ml of water, 40 ml of dioxane and 2.84 g (10 mmol) of Compound 40. The temperature was lowered to 0° C. in an ice bath, and 2.78 g (22 mmol) of dimethyl sulfate was added dropwise. Reaction was carried out for 24 hours while increasing the temperature to room temperature. Additional 1.26 g (10 mmol) of dimethyl sulfate was added dropwise to the reaction liquid, and reaction was performed for 8.5 hours at room temperature. The reaction liquid was combined with 100 ml of purified water and was extracted once with 100 ml of toluene and then twice with 50 ml of toluene. The organic phase was dried over MgSO$_4$ and was distilled under reduced pressure to remove the solvent. The distillate was dissolved in 100 ml of dichloromethane, and 10 ml of trifluoroacetic acid was added, followed by reaction for 20 hours at room temperature. The reaction liquid was combined with 100 ml of saturated NaHCO$_3$ water and the organic phase was extracted. The organic phase was washed with purified water, then dried over MgSO$_4$ and distilled under reduced pressure to remove the solvent, giving a crude product. The crude product was purified by silica gel column chromatography (eluting solution: hexane/ethyl acetate=19/1) to afford 0.338 g of Compound 41 (12% yield, white solid).

The product was analyzed, and the results were as follows.

$^1$H NMR (δ, CDCl$_3$): 7.33-7.00 (m, 6H, Ar—H), 6.87-6.74 (m, 2H, Ar—H), 4.17 (br, 2H, NH$_2$), 2.62 (s, 6H, CH$_3$).

(Synthesis of Compound 42)

[Chem. 64]

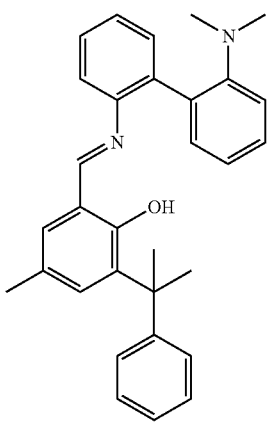

Compound 42

In a thoroughly dried 100 ml eggplant flask (equipped with a three-way cock and a magnetic stirrer), 0.223 g (5.25 mmol) of Compound 41 and 0.254 g (1.0 mmol) of 2-hydroxy-5-methyl-3-adamantyl benzaldehyde were dissolved in 5 ml of ethanol. Further, one droplet of acetic acid was added, and reaction was carried out for 16 hours at room temperature. The reaction liquid was distilled under reduced pressure to remove the solvent. The distillate was recrystallized in ethanol to afford 0.380 g of Compound 42 (85% yield, yellow solid).

The product was analyzed, and the results were as follows.
$^1$H NMR (δ, CDCl$_3$): 12.77 (s, 1H, OH), 8.24 (s, 1H, N=CH), 7.36-7.03 (m, 12H, Ar—H), 6.90-6.85 (m, 2H, Ar—H), 6.94 (d, 1H, Ar—H), 2.30 (s, 3H, CH$_3$), 2.20 (s, 6H, CH$_3$), 1.64 (s, 6H, C(CH$_3$)$_2$)

(Synthesis of Compound 43)

[Chem. 65]

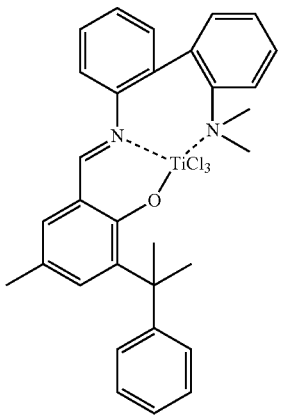

Compound 43

A thoroughly dried 100 ml eggplant flask (equipped with a three-way cock and a magnetic stirrer) was charged with 0.234 g (0.7 mmol) of TiCl$_4$(thf)$_2$ and 5 ml of THF. The mixture was cooled to −78° C. in a dry ice/methanol bath. Separately, 0.314 g (0.7 mmol) of Compound 42 was dissolved in 2.5 ml of THF. The resultant solution was added dropwise to the mixture. Reaction was carried out for 13 hours while increasing the temperature to room temperature. The solid that precipitated after the reaction was filtered out, then washed with 20 ml of pentane and dried to give 0.321 g of Compound 43 (76% yield, orange solid).

The product was analyzed, and the results were as follows.
FD-MS: m/z=602 (M$^+$, C$_{31}$H$_{31}$Cl$_3$N$_2$OTi)

Example 33

(Synthesis of Compound 44)

[Chem. 66]

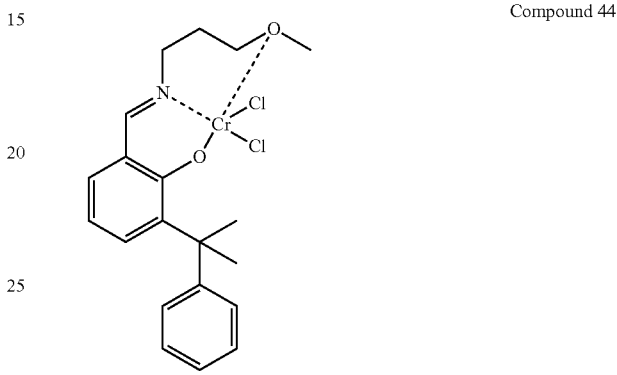

Compound 44

In a thoroughly dried 50 ml two-necked eggplant flask (equipped with a three-way cock and a magnetic stirrer), 311 mg (1.0 mmol) of Compound 1 was dissolved in 10 ml of diethyl ether. The mixture liquid was cooled to −78° C., and 0.63 ml (1.0 mmol) of 1.6 mol/L hexane solution of n-butyllithium was added dropwise. Reaction was carried out for 1 hour while gradually increasing the temperature to room temperature. To the reaction liquid, 1.0 ml (1.0 mmol) of 1.0 mol/L tetrahydrofuran solution of chromium trichloride was added dropwise at −78° C. Reaction was carried out for 4 hours while gradually increasing the temperature to room temperature. The reaction liquid was then concentrated to approximately 5 ml, and 20 ml of pentene was added thereto to precipitate a solid. The solid was filtered out and was washed with pentene. Consequently, 302 mg of Compound 44 was obtained (64% yield, brown solid).

Example 34

A thoroughly nitrogen-purged 100 ml autoclave was charged with 28 ml of toluene and subsequently with 1.0 mmol in terms of aluminum atom of methylaluminoxane (MAO, 1M toluene solution). Further, 0.001 mmol of Compound 2 (1 mM toluene solution) was added. The system was pressurized with ethylene at 0.8 MPa-G, and thereby reaction was initiated. The reaction was carried out for 30 minutes at 25 to 28° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene with use of a liquid nitrogen trap under reduced pressure. The products were analyzed by gas chromatography. The selectivity for 1-hexene with respect to all the products was 35%. The products included trace amounts of 1-octene and decenes. The selectivity for polyethylene was 65%. The catalytic activity was calculated from the total amount of the products to be 0.08 kg-products/(mmol-Ti·h).

Examples 35 to 64

Reaction was carried out in the same manner as in Example 34, except that Compound 2 was replaced by Compound 5, 7, 9, 11 or any one of 13 to 38. The results are shown in Table 1.

TABLE 1

| | | Selectivity (wt %) | | | Activity |
|---|---|---|---|---|---|
| | Compound used | 1-Hexene | De-cenes | Polyethylene | [kg-products/(mmol-Ti · h)] |
| Ex. 35 | Compound 5 | 87 | 11 | 2 | 5.9 |
| Ex. 36 | Compound 7 | 86 | 12 | 2 | 6.1 |
| Ex. 37 | Compound 9 | 92 | 6 | 2 | 3.9 |
| Ex. 38 | Compound 11 | 58 | Trace | 42 | 0.1 |
| Ex. 39 | Compound 13 | 43 | 47 | 10 | 0.9 |
| Ex. 40 | Compound 14 | 89 | 9 | 2 | 4.1 |
| Ex. 41 | Compound 15 | 77 | Trace | 23 | 0.1 |
| Ex. 42 | Compound 16 | 80 | 9 | 11 | 1.2 |
| Ex. 43 | Compound 17 | 87 | 8 | 5 | 3.9 |
| Ex. 44 | Compound 18 | 87 | 8 | 5 | 4.8 |
| Ex. 45 | Compound 19 | 73 | 25 | 2 | 5.3 |
| Ex. 46 | Compound 20 | 92 | Trace | 8 | 0.6 |
| Ex. 47 | Compound 21 | 15 | Trace | 85 | 0.1 |
| Ex. 48 | Compound 22 | 88 | 5 | 7 | 3.3 |
| Ex. 49 | Compound 23 | 86 | 9 | 5 | 3.5 |
| Ex. 50 | Compound 24 | 87 | 12 | 1 | 4.2 |
| Ex. 51 | Compound 25 | 92 | 7 | 1 | 4.8 |
| Ex. 52 | Compound 26 | 92 | 6 | 2 | 4.6 |
| Ex. 53 | Compound 27 | 92 | 7 | 1 | 4.8 |
| Ex. 54 | Compound 28 | 86 | 8 | 6 | 3.4 |
| Ex. 55 | Compound 29 | 85 | 11 | 4 | 3.6 |
| Ex. 56 | Compound 30 | 82 | 12 | 6 | 4.4 |
| Ex. 57 | Compound 31 | 89 | 5 | 6 | 3.3 |
| Ex. 58 | Compound 32 | 87 | 6 | 7 | 2.5 |
| Ex. 59 | Compound 33 | 80 | 15 | 5 | 2.9 |
| Ex. 60 | Compound 34 | 76 | 20 | 4 | 1.1 |
| Ex. 61 | Compound 35 | 89 | 6 | 6 | 2.2 |
| Ex. 62 | Compound 36 | 24 | Trace | 76 | 0.3 |

Example 65

A thoroughly nitrogen-purged 100 ml autoclave was charged with 28 ml of toluene and subsequently with 1.0 mmol in terms of aluminum atom of methylaluminoxane (MAO, 1 M toluene solution). Further, 0.001 mmol of Compound 43 (1 mM toluene solution) was added. The system was pressurized with ethylene at 0.8 MPa-G, and thereby reaction was initiated. The reaction was carried out for 30 minutes at 25 to 28° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene (dry weight: 148 mg) with use of a liquid nitrogen trap under reduced pressure. The products were analyzed by gas chromatography. The low-boiling fraction consisted solely of 1-hexene (3.6 mg).

Example 66

A thoroughly nitrogen-purged 100 ml autoclave was charged with 28 ml of toluene and subsequently with 1.0 mmol in terms of aluminum atom of methylaluminoxane (MAO, 1 M toluene solution). Further, 0.001 mmol of Compound 44 (1 mM toluene solution) was added. The system was pressurized with ethylene at 0.8 MPa-G, and thereby reaction was initiated. The reaction was carried out for 30 minutes at 25 to 28° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene (dry weight: 5.1 mg) with use of a liquid nitrogen trap under reduced pressure. The products were analyzed by gas chromatography. The low-boiling fraction consisted solely of 1-hexene (0.2 mg).

Comparative Example 1

A thoroughly nitrogen-purged 100 ml autoclave was charged with 28 ml of toluene and subsequently with 1.0 mmol in terms of aluminum atom of methylaluminoxane (MAO, 1 M toluene solution). Further, 0.001 mmol of Compound 45 (1 mM toluene solution) illustrated below according to WO 01/44324 was added. The system was pressurized with ethylene at 0.8 MPa-G, and thereby reaction was initiated. The reaction was carried out for 30 minutes at 25 to 40° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from polyethylene with use of a liquid nitrogen trap under reduced pressure. According to gas chromatography, 298 mg of polyethylene resulted. However, 1-hexene was not detected.

[Chem. 67]

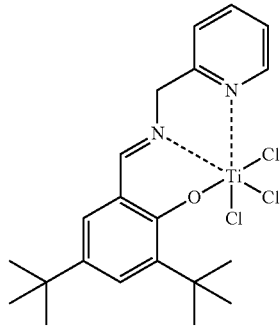

Compound 45

Comparative Example 2

A thoroughly nitrogen-purged 100 ml autoclave was charged with 28 ml of toluene and subsequently with 1.0 mmol in terms of aluminum atom of methylaluminoxane (MAO, 1 M toluene solution). Further, 0.001 mmol of Compound 46 (1 mM toluene solution) illustrated below according to Chemistry Letters, 1999, pp. 1065-1066 was added. The system was pressurized with ethylene at 0.8 MPa-G, and thereby reaction was initiated. The reaction was carried out for 10 minutes at 25 to 40° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from polyethylene with use of a liquid nitrogen trap under reduced pressure. According to gas chromatography, 2.54 g of polyethylene resulted. However, 1-hexene was not detected.

[Chem. 68]

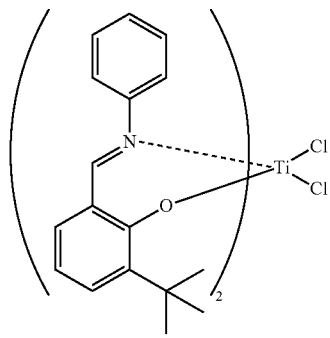

Compound 46

Example 67

A thoroughly nitrogen-purged 500 ml autoclave was charged with 144 ml of cyclohexane and subsequently with 5.0 mmol in terms of aluminum atom of methylaluminoxane (MMAO-3A manufactured by Tosoh Finechem Corporation, 1 M hexane solution). Further, 0.0005 mmol of Compound 9 (0.5 mM toluene solution) was added. The system was pressurized with ethylene at 3.2 MPa-G, and thereby reaction was initiated. The reaction was carried out for 60 minutes at 25 to 32° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene with use of a liquid nitrogen trap under reduced pressure. The products were analyzed by gas chromatography. Polyethylene that attached to the agitating blade of the reactor was collected (0.48 g). The selectivity for 1-hexene with respect to all the products was 93%. The selectivity for decenes was 6%, and that for polyethylene was 1%. The catalytic activity was calculated from the total amount of the products to be 114 kg-products/(mmol-Ti·h)

Example 68

A thoroughly nitrogen-purged 500 ml autoclave was charged with 144 ml of n-pentane and subsequently with 5.0 mmol in terms of aluminum atom of methylaluminoxane (MMAO-3A manufactured by Tosoh Finechem Corporation, 1 M hexane solution). Further, 0.0005 mmol of Compound 9 (0.5 mM toluene solution) was added. The system was pressurized with ethylene at 3.2 MPa-G, and thereby reaction was initiated. The reaction was carried out for 60 minutes at 25 to 32° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene with use of a liquid nitrogen trap under reduced pressure. The products were analyzed by gas chromatography. Polyethylene that attached to the agitating blade of the reactor was collected (0.09 g). The selectivity for 1-hexene with respect to all the products was 94%. The selectivity for decenes was 5%, and that for polyethylene was 1%. The catalytic activity was calculated from the total amount of the products to be 114 kg-products/(mmol-Ti·h).

Example 69

A thoroughly nitrogen-purged 500 ml autoclave was charged with 144 ml of n-pentane and 0.3 mg of Adeka Pluronic L 72, and subsequently with 5.0 mmol in terms of aluminum atom of methylaluminoxane (MMAO-3A manufactured by Tosoh Finechem Corporation, 1 M hexane solution). Further, 0.0005 mmol of Compound 9 (0.5 mM toluene solution) was added. The system was pressurized with ethylene at 3.2 MPa-G, and thereby reaction was initiated. The reaction was carried out for 60 minutes at 25 to 32° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene with use of a liquid nitrogen trap under reduced pressure. The products were analyzed by gas chromatography. Polyethylene did not attach to the agitating blade of the reactor. The selectivity for 1-hexene with respect to all the products was 93%. The selectivity for decenes was 6%, and that for polyethylene was 1%. The catalytic activity was calculated from the total amount of the products to be 89 kg-products/(mmol-Ti·h).

Example 70

A thoroughly nitrogen-purged 500 ml autoclave was charged with 144 ml of n-pentane and subsequently with 5.0 mmol in terms of aluminum atom of methylaluminoxane (MMAO-3A manufactured by Tosoh Finechem Corporation, 1 M hexane solution). Further, 0.0005 mmol of Compound 9 (0.5 mM toluene solution) was added. The system was pressurized with ethylene and hydrogen at 3.2 MPa-G and 0.1 MPa-G, respectively, and thereby reaction was initiated. The reaction was carried out for 60 minutes at 25 to 32° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene with use of a liquid nitrogen trap under reduced pressure. The products were analyzed by gas chromatography. Polyethylene did not attach to the agitating blade of the reactor. The selectivity for 1-hexene with respect to all the products was 92%. The selectivity for decenes was 7%, and that for polyethylene was 1%. The catalytic activity was calculated from the total amount of the products to be 84 kg-products/(mmol-Ti·h).

Example 71

(Preparation of Carrier 1)

A thoroughly nitrogen-purged 300 ml flask was charged with 6.2 g (1.0 mol) of porous silica (H-31 manufactured by ASAHI GLASS CO., LTD.) and 80 ml of toluene. While maintaining the liquid temperature at 15° C., 120 ml of methylaluminoxane (MAO, 1 M toluene solution) was added dropwise. The liquid temperature was then increased to 95° C., and reaction was performed for 60 minutes with heating. After the completion of the reaction, the solid was collected by filtration and sufficiently washed with toluene, and was added to toluene to give a toluene slurry of Carrier 1.

Part of the Carrier 1 toluene slurry-prepared as described above was dried and analyzed for composition, resulting in the finding that Carrier 1 contained 27.9 wt % of aluminum.
(Oligomerization)

The Carrier 1 toluene slurry in an amount that contained 0.15 mmol in terms of aluminum atom of Carrier 1 and 4 ml of toluene, and 0.0005 mmol of Compound 9 were stirred for 1 hour at room temperature, resulting in a catalyst slurry. A thoroughly nitrogen-purged 500 ml autoclave was charged with 145 ml of n-pentane and subsequently with 0.05 mmol in terms of aluminum atom of trioctylaluminum (0.1M decane solution), and the mixture was stirred. The catalyst slurry was added to the autoclave. The system was pressurized with ethylene at 4.5 MPa-G, and thereby reaction was initiated. The reaction was carried out for 60 minutes at 45 to 52° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene with use of a liquid nitrogen trap under reduced pressure. The products were analyzed by gas chromatography. The selectivity for 1-hexene with respect to all the products was 87%. The selectivity for decenes was 11%, and that for polyethylene was 2%. The catalytic activity was calculated from the total amount of the products to be 104 kg-products/(mmol-Ti·h).

Example 72

(Preparation of Carrier 2)

95.2 g (1.0 mol) of anhydrous magnesium chloride, 442 ml of decane and 390.6 g (3.0 mol) of 2-ethylhexyl alcohol were reacted at 130° C. for 2 hours to give a uniform solution. 25 ml of the uniform solution (25 mmol in terms of magnesium atom) was placed into a thoroughly nitrogen-purged 200 ml flask, and 100 ml of purified decane was added for dilution.

While maintaining the liquid temperature at 15° C., 26 mmol of triethylaluminum was added dropwise. The liquid temperature was then increased to 80° C., and additional 49 mmol of triethylaluminum was added dropwise. Reaction was performed for 150 minutes with heating. After the completion of the reaction, the solid was collected by filtration and sufficiently washed with toluene, and was added to toluene to give a toluene slurry of Carrier 2.

Part of the Carrier 2 toluene slurry prepared as described above was dried and analyzed for composition, resulting in the finding that Carrier 2 contained 17.0 wt % of magnesium and 2.9 wt % of aluminum.
(Oligomerization)

The Carrier 2 toluene slurry in an amount that contained 0.15 mmol in terms of aluminum atom of Carrier 2 and 4 ml of toluene, and 0.0005 mmol of Compound 9 were stirred for 1 hour at room temperature, resulting in a catalyst slurry. A thoroughly nitrogen-purged 500 ml autoclave was charged with 145 ml of n-pentane and subsequently with 0.05 mmol in terms of aluminum atom of trioctylaluminum (0.1 M decane solution), and the mixture was stirred. The catalyst slurry was added to the autoclave. The system was pressurized with ethylene at 4.5 MPa-G, and thereby reaction was initiated. The reaction was carried out for 60 minutes at 35 to 42° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene (dry weight: 1.63 g) with use of a liquid nitrogen trap under reduced pressure. The products were analyzed by gas chromatography. The low-boiling fraction consisted of 1-hexene (0.44 g) and decenes (0.09 g).

Example 73

The Carrier 1 toluene slurry in an amount that contained 0.15 mmol in terms of aluminum atom of Carrier 1 and 4 ml of toluene, and 0.0005 mmol of Compound 9 were stirred for 1 hour at room temperature, resulting in a catalyst slurry. A thoroughly nitrogen-purged 500 ml autoclave was charged with 145 ml of n-heptane and subsequently with 0.05 mmol in terms of aluminum atom of trioctylaluminum (0.1 M decane solution), and the mixture was stirred. The catalyst slurry was added to the autoclave. The system was pressurized with ethylene and hydrogen at partial pressures of 4.5 MPa-G and 0.1 MPa-G, respectively, and thereby reaction was initiated. The reaction was carried out for 60 minutes at 45 to 52° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene with use of a liquid nitrogen trap under reduced pressure. The products were analyzed by gas chromatography. The selectivity for 1-hexene with respect to all the products was 88%. The selectivity for decenes was 11%, and that for polyethylene was 1%. The catalytic activity was calculated from the total amount of the products to be 102 kg-products/(mmol-Ti·h).

Example 74

The Carrier 1 toluene slurry in an amount that contained 0.15 mmol in terms of aluminum atom of Carrier 1 and 4 ml of toluene, and 0.0005 mmol of Compound 9 were stirred for 1 hour at room temperature, resulting in a catalyst slurry. A thoroughly nitrogen-purged 500 ml autoclave was charged with 98.1 g of 1-hexene and subsequently with 0.05 mmol in terms of aluminum atom of trioctylaluminum (0.1 M decane solution), and the mixture was stirred. The catalyst slurry was added to the autoclave. The system was pressurized with ethylene at 4.5 MPa-G, and thereby reaction was initiated. The reaction was carried out for 60 minutes at 45 to 52° C. while maintaining the pressure by supplying ethylene. The reaction was then terminated by adding a small amount of isopropanol. The reaction liquid was washed with 0.1 N hydrochloric acid and purified water. Low-boiling fractions (having 10 or less carbon atoms) were separated from high-boiling fractions and polyethylene with use of a liquid nitrogen trap under reduced pressure. The products were analyzed by gas chromatography. The weight of 1-hexene that was recovered was 143.9 g. The reaction also produced 9.4 g of decenes and 1.3 g of polyethylene.

The invention claimed is:

1. A transition metal complex compound [A] represented by Formula (I) below:

[Chem. 1]

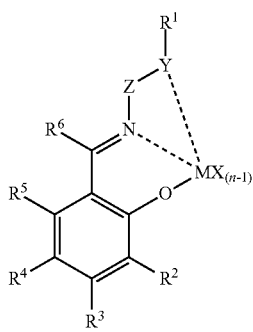

(I)

wherein $R^1$ to $R^6$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, two or more of $R^1$ to $R^6$ may be linked to each other, and $R^1$ may be linked to Z;

M is a transition metal atom of Group 3 to Group 10 of the periodic table;

n is a valence of M;

X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, the atoms or groups indicated by X may be the same or different from each other, and the groups indicated by X may be linked to each other to form a ring;

Y is an oxygen atom, a nitrogen atom, a phosphorus atom or a sulfur atom;

Z is a hydrocarbon group or a heterocyclic compound residue that may have a substituent group, and the minimum number of bonds linking Y with N is 5 or 6;

the bond between Y and Z may be a double bond or a triple bond, and the bond between Y and $R^1$ may be a double bond or a triple bond; and the dotted lines each denote a coordination bond.

2. The transition metal complex compound [A] according to claim 1, wherein Y, N and Z in the transition metal complex compound of Formula (I) form a structure represented by Formula (II) below:

[Chem. 2]

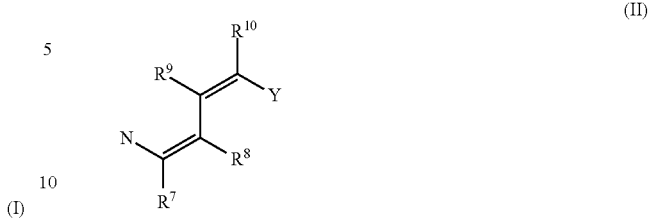

(II)

wherein Y is an oxygen atom, a nitrogen atom, a phosphorus atom or a sulfur atom; and $R^7$ to $R^{10}$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and when $R^7$ to $R^{10}$ are hydrocarbon groups, $R^7$ and $R^8$ may be linked to each other to form a ring and $R^9$ and $R^{10}$ may be linked to each other to form a ring.

3. The transition metal complex compound [A] according to claim 1, wherein M in the transition metal complex compound of Formula (I) is a transition metal atom of Group 4 of the periodic table, and n is 4.

4. An olefin oligomerization catalyst comprising the transition metal complex compound [A] described in claim 1.

5. The olefin oligomerization catalyst according to claim 4, wherein the catalyst comprises:

[A] the transition metal complex compound; and

[B] at least one compound selected from the group consisting of (b-1) an organometallic compound, (b-2) an organoaluminum oxy-compound and (b-3) a compound which reacts with the transition metal complex compound [A] to form an ion pair.

6. The olefin oligomerization catalyst according to claim 4, wherein the catalyst comprises:

[A] the transition metal complex compound;

[B] at least one compound selected from the group consisting of (b-1) an organometallic compound, (b-2) an organoaluminum oxy-compound and (b-3) a compound which reacts with the transition metal complex compound [A] to form an ion pair; and

[C] a carrier to support at least one compound selected from [A] and [B].

7. A process for producing an olefin oligomer, comprising oligomerizing an olefin in the presence of the olefin oligomerization catalyst described in claim 4.

8. The process according to claim 7, wherein the olefin is ethylene.

9. The process according to claim 7, wherein the olefin is ethylene and the olefin oligomer is 1-hexene.

10. A process for producing an olefin oligomer, comprising oligomerizing an olefin in the presence of the olefin oligomerization catalyst described in claim 4 and with a C5-7 linear saturated hydrocarbon as a solvent.

11. A process for producing an olefin oligomer, comprising oligomerizing an olefin in the presence of the olefin oligomerization catalyst described in claim 4 and hydrogen.

12. A process for producing an olefin oligomer, comprising oligomerizing an olefin in the presence of the olefin oligomerization catalyst described in claim 4 and an antistatic agent.

13. A transition metal complex compound [A] represented by Formula (I') below:

[Chem. 3]

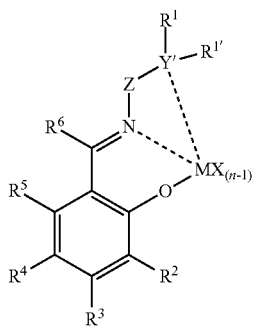

(I')

wherein $R^1$ to $R^6$ and $R^{1'}$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, two or more of $R^{1'}$ and $R^1$ to $R^6$ may be linked to each other, and $R^1$ may be linked to Z;

M is a transition metal atom of Group 3 to Group 10 of the periodic table;

n is a valence of M;

X is a hydrogen atom, a halogen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group, the atoms or groups indicated by X may be the same or different from each other, and the groups indicated by X may be linked to each other to form a ring;

Y' is a nitrogen atom or a phosphorus atom;

Z is a hydrocarbon group or a heterocyclic compound residue that may have a substituent group, and the minimum number of bonds linking Y' with N is 5 or 6; and the dotted lines each denote a coordination bond.

14. The transition metal complex compound [A] according to claim 13, wherein Y', N and Z in the transition metal complex compound of Formula (I') form a structure represented by Formula (II') below:

[Chem. 4]

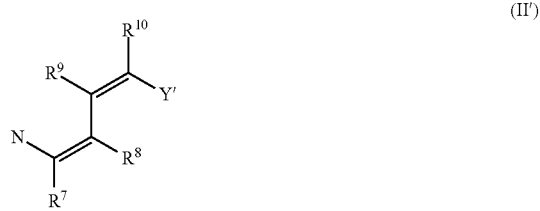

(II')

wherein Y' is a nitrogen atom or a phosphorus atom; and
$R^7$ to $R^{10}$ are the same or different from each other and are each a hydrogen atom, a halogen atom, a hydrocarbon group, a heterocyclic compound residue, an oxygen-containing group, a nitrogen-containing group, a boron-containing group, an aluminum-containing group, a sulfur-containing group, a phosphorus-containing group, a silicon-containing group, a germanium-containing group or a tin-containing group, and when $R^7$ to $R^{10}$ are hydrocarbon groups, $R^7$ and $R^8$ may be linked to each other to form a ring and $R^9$ and $R^{10}$ may be linked to each other to form a ring.

15. The transition metal complex compound [A] according to claim 13, wherein M in the transition metal complex compound of Formula (1') is a transition metal atom of Group 4 of the periodic table, and n is 4.

* * * * *